United States Patent [19]

Stamler et al.

[11] Patent Number: 5,385,937
[45] Date of Patent: Jan. 31, 1995

[54] NITROSATION OF HOMOCYSTEINE AS A METHOD FOR TREATING HOMOCYSTEINEMIA

[75] Inventors: Jonathan Stamler, Boston; Joseph Loscalzo, Dedham, both of Mass.

[73] Assignee: Brigham & Women's Hospital, Boston, Mass.

[21] Appl. No.: 839,188

[22] Filed: Feb. 21, 1992

Related U.S. Application Data

[63] Continuation-in-part of Ser. No. 683,415, Apr. 10, 1991, abandoned.

[51] Int. Cl.$^6$ ................ A01N 37/00; A61K 31/19
[52] U.S. Cl. .................................................. 514/557
[58] Field of Search ........................................ 514/557

[56] References Cited

U.S. PATENT DOCUMENTS 4,778,787 10/1988 Catsimpoolas et al. .............. 514/25
5,002,964  3/1991 Loscalzo ............................ 514/423

OTHER PUBLICATIONS

Kang, Soo-Sang, et al., *The American Society for Clinical Investigation, Inc.*, 77:1482-1486, (May 1986).
Aldred et al., *J. Chem. Soc. Perking Trans. II*: 777-782 (1982).
Brattström et al., *Atherosclerosis* 81:51-60 (1990).
Brattström, L. E. et al., *Metabolism* 34 (11):1073-1077 (1985).
Clarke et al., *N. Engl. J. Med.* 324:1149-1155 (1991).
Cooke et al., *Am. J. Physiol.* 28:H804-H812 (1990).
Davis et al., *Am. J. Dis. Child* 129:1020-1021 (1975).
Gordon et al., *Lancet* 339:25-26 (1992).
Graeber et al., *Pediatr. Res.* 16:490-493 (1982).
Grossman et al., *Anal. Biochem.* 179:28-33 (1989).
Harker et al., *J. Clin. Invest.* 58:731-741 (1976).
Harker et al., *N. Engl. J. Med.* 291:537-543 (1974).
Heinecke et al., *J. Biol. Chem.* 262:10098-10103 (1987).
Henry et al., *Br. J. Pharmacol.* 98:757-766 (1989).
Ignarro et al., *Proc. Natl. Acad. Sci., USA* 84:9265-9269 (1987).
Ignarro, *Circ. Res.* 65:1-21 (1989).
James, *J. Am. Coll. Cardiol.* 15:763-774 (1990).
Kowaluk et al., *J. Pharmacol. Exp. Ther.* 255:1256-1264 (1990).
Malinow et al., *Circulation* 79:1180-1188 (1989).
McCully et al., *Res. Comm. Chem. Path. Pharm.* 56(3):349-360 (1987).
McCully et al., *Am. J. Path.* 61(1):1-8 (1970).
McCully, *Nature* 231:391-92 (1971).
McDonald et al., *Lancet* 1:745-746 (1964).
Osborne et al., *J. Clin. Invest.* 83:465-473 (1989).
Palmer et al., *Nature* 327:524-526 (1987).
Parthasarathy, *Biochim. Biophys. Acta* 917:337-340 (1987).
Riegel et al., *J. Biol. Chem.* 112:149-154 (1935).
Root et al., *J. Clin. Invest.* 55:945-955 (1975).
Skovby, *Haemotasis* 19 (Supp. 1):4-9 (1989).
Stamler et al., *Circ. Res.* 65:789-795 (1989).
Stamler et al., *Clinical Research* 38(2):246A Abstract (1990).
Stamler et al., *Am. J. Cardiol.* 62:377-380 (1988).
Starkebaum et al., *J. Clin. Invest.* 77:1370-1376 (1986).
Thomas et al., *Thromb Res.* 44:859-866 (1986).
Wall et al., *Thromb. Res.* 18:113-121 (1980).
Zucker et al., *Thromb. Haenostas (Stuttgart)* 51: 119-124 (1984).

*Primary Examiner*—Johann Righter
*Assistant Examiner*—Rebecca Cook
*Attorney, Agent, or Firm*—Charles J. Herron; Elliot M. Olstein

[57] ABSTRACT

Administration of a nitrosating compound, such as nitroglycerin, nitric oxide, S-nitrosothiol, S-nitrosoprotein, nitroprusside, sydnonimines, furoxans, nitrosonium salts, and related compounds is used for the treatment or prevention of disease states resulting from hyperhomocysteinemia. The disease states include vascular, ocular, skeletal, neurological, and cytotoxicity disorders. In addition, nitrosating compounds may also be administered for the treatment or prevention of disease states resulting from other sulfur-containing amino acids, such as cysteine.

4 Claims, 12 Drawing Sheets

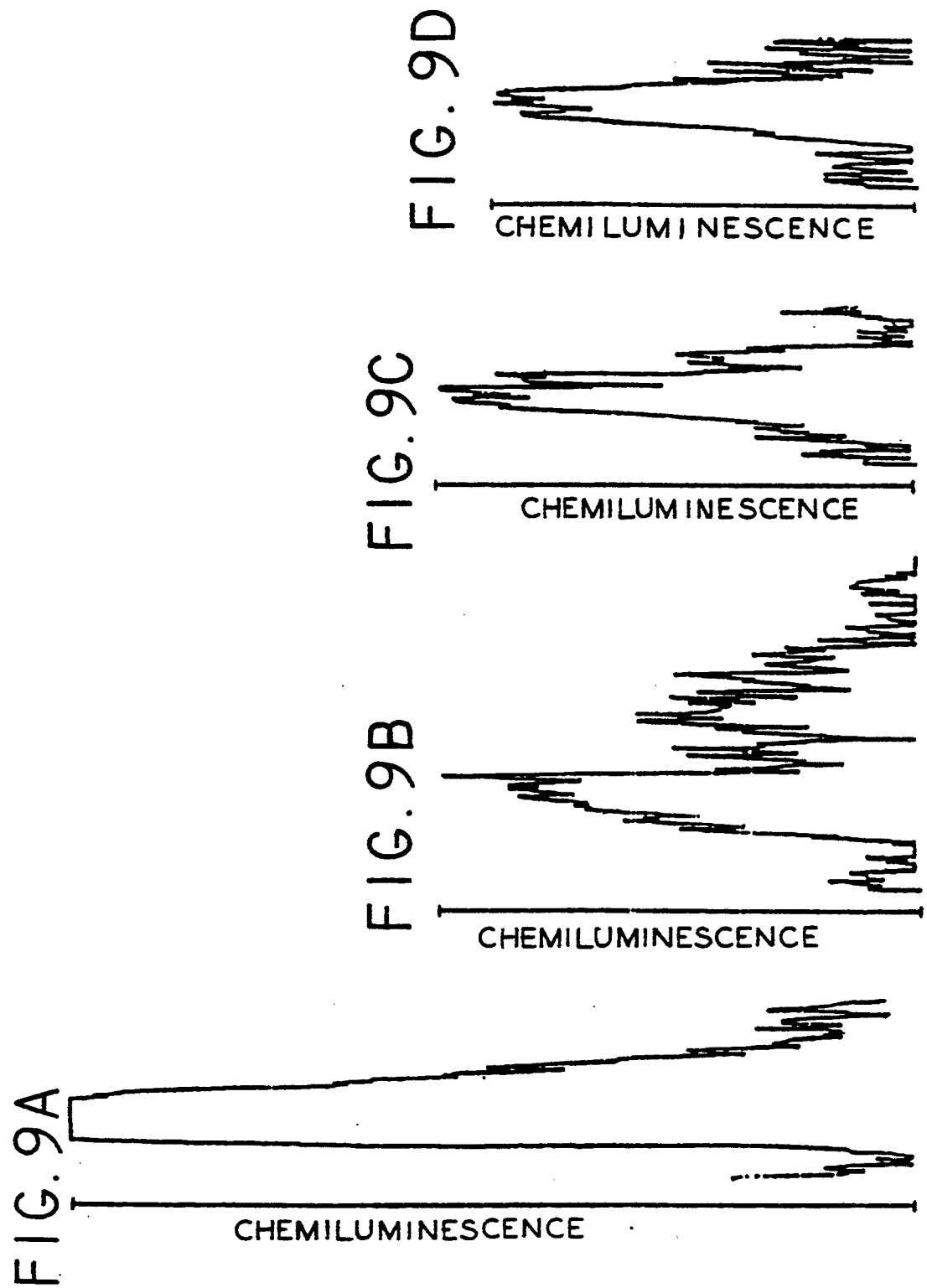

NITROSATION OF HOMOCYSTEINE AS A METHOD FOR TREATING HOMOCYSTEINEMIA

CROSS-REFERENCE TO RELATED APPLICATION

This application is a continuation-in-part of U.S. application Ser. No. 07/683,415, filed Apr. 10, 1991 now abandoned.

BACKGROUND OF THE INVENTION

This invention was made with government support under R01HL40411, HL43344 and RR04870 awarded by the National Institutes of Health. The government has certain rights in the invention.

1. Field of the Invention

This invention relates to a new method for the treatment or prevention of disease states associated with elevated levels of homocysteine, comprising administering a pharmaceutical composition containing a nitrosating compound to a patient.

2. Brief Description of the Background Art

Homocysteine is a thiol-containing amino acid that results from the demethylation of methionine. Homocysteine is readily oxidized in body fluids to homocysteine disulfide (homocystine), mixed disulfides, and the cyclized oxidation product, homocysteine thiolactone (HTL).

Homocystinurias are clinical disorders which result from a number of different inborn or acquired defects in the pathway which control homocysteine metabolism. These disorders are characterized by increased concentrations of homocystine in the blood and urine.

The most common form of homocystinuria results from a deficiency of cystathionine $\beta$-synthase, an enzyme in the transsulfuration pathway by which methionine is converted to cysteine. Another form results from a deficiency of 5,10-methyl tetrahydrofolate reductase, which provides substrate for the $B_{12}$-dependent conversion of homocysteine to methionine. Homocystinurias also result from deficiencies of necessary metabolic cofactors, such as folate, and vitamins $B_{12}$ and $B_6$. In addition, homocystinuria may result from bile acid sequestrant plus niacin therapy which impairs folate absorption. Finally, these disorders may also be secondary to abnormal kidney function, or to other mechanisms not yet characterized.

In some patients, metabolic defects may cause elevations of homocysteine in serum which are not high enough to cause the excretion of detectable amounts of homocystine in the urine, yet result in serious pathological consequences. Thus, investigators have suggested the term "hyperhomocysteinemia" to refer to a transient or persistent elevation of serum homocysteine, which may or may not be accompanied by increased homocystine in the urine (Malinow et al. Circulation 79:1180-1188 (1989)).

Hyperhomocysteinemia causes a variety of disease states which manifest in serious vascular, ocular, neurological, and skeletal abnormalities.

Atherogenesis and thrombosis are well-recognized complications of hyperhomocysteinemia. (Clarke et al., N. Engl. J. Med. 324:1149–1155 (1991); Malinow, Circulation 81:2004–2006 (1990)). Afflicted individuals often experience serious thrombotic complications at an early age, with thrombosis of extracranial and intracranial arteries, veins and sinuses, as well as coronary occlusion, being common fatal occurrences. In young patients, occlusion of peripheral arteries often results in renal vascular hypertension, intermittent claudication or mesenteric ischemia, and thrombosis may be followed by pulmonary embolism. If left untreated, juvenile hyperhomocysteinemia results in the death of more than 50% of the affected individuals before the age or 20, due to myocardial infarction, stroke or pulmonary embolism (Brattström, L. E. et al., Metabolism 34(11):1073-1077 (1985)). In older patients, moderate hyperhomocysteinemia is found to exist in 20-30% of those afflicted with coronary and peripheral vascular disease (Malinow, M. R., Circulation 81:2004–2006 (1990)).

Normal hemostasis is a dynamic process in which platelet aggregates form and disperse continuously. To achieve this process, physiologic stimuli for platelet activation are counterbalanced by vascular endothelial cell secretion of such substances as prostacyclin and endothelium-derived relaxing factor (EDRF), which has been identified as nitric oxide (NO), or a closely related derivative thereof (Palmer et al., Nature 327:524–526 (1987); Ignarro et al., Proc. Natl. Acad. Sci., USA 84:9265–9269 (1987)). Accordingly, endothelial dysfunction or injury may predispose an individual to thrombosis and vascular occlusive events.

Inferential evidence has suggested the existence of a causal mechanism for endothelial dysfunction and enhanced platelet aggregation in hyperhomocysteinemia. Marked platelet accumulation at sites of vascular injury and platelet-rich occlusive thrombi are distinctive pathological features of both human and experimental hyperhomocysteinemia (James, JACC 15:763-774 (1990); Harker et al., N. Engl. J. Med. 291:537-543 (1974); Harker et al., J. Clin. Invest. 58:731-741 (1976)). To explain this pathologic appearance, several groups have reported direct pro-aggregatory effects of homocysteine and HTL (McDonald et al., Lancet 1:745–746 (1964); Graeber et al., Pediatr. Res. 16:490–493 (1982); McCully et al., Res. Comm. Chem. Path. Pharm. 56(3):349–360 (1987)). However, these pro-aggregatory actions have not been demonstrated with uniformity, and supportive biochemical and molecular mechanisms have not been well elucidated. Moreover, the platelet-activating effects of homocysteine, attributed to its reactive SH group, are difficult to reconcile with the known anti-platelet properties of other biological thiols with similar chemical and physical characteristics. For example, it has been shown that glutathione, cysteine, and N-acetylcysteine have anti-platelet effects, at millimolar concentrations (Thomas et al., Thromb Res. 44:859–866 (1986); Stamler et al., Am. J. Cardiol. 62:377-380 (1988)).

Other investigators have suggested that homocysteine-induced endothelial injury, by exposing sub-endothelial connective tissue, represents an alternative mechanism for platelet activation in vivo (Harker et al., N. Engl. J. Med. 291:537-543 (1974); Harker et al., J. Clin. Invest. 58:731-741 (1976)). Endothelial toxicity has subsequently been confirmed, and attributed to $H_2O_2$, generated by way of the SH group, or to the direct toxic effects of HTL (Wall et al., Thromb. Res. 18:113–121 (1980); Starkebaum et al., J. Clin. Invest. 77:1370-1376 (1986); McCully et al., Am. J. Path. 61(1):1-8 (1970)). In addition, high levels of oxidation products of homocysteine may further significantly increase the homocysteine-related burden in plasma and the cell cytosol, and thereby contribute to its pathogenicity (Kang et al., Am. Soc. Clin. Invest. 77:1482–1486 (1986); McCully, Nature (London) 231:391–92 (1971)). Others have proposed that homocysteine potentiates the auto-oxidation of low-density lipoprotein cholesterol and promotes thrombosis through enhanced platelet aggregation.

In addition to its thrombogenic and atherogenic effects, homocysteine interferes with the normal cross-linking of collagen. This effect is responsible, not only for the vascular, but also for the ocular, skeletal and neurological complications of hyperhomocysteinemia. For example, altered collagen in the suspensory ligament of the optic lens causes dislocated lenses (ectopia lentis), and in the bone matrix, results in osteoporosis.

Neurological complications of homocysteine include delayed psychomotor development, severe mental retardation, seizures, and upper motor neuron dysfunction. While recurrent cerebrovascular accidents secondary to thrombotic disorders may be responsible for the mental retardation and other neurological complications, direct chemical cytotoxic effects on cerebral cell metabolism have also been implicated. Furthermore, widespread pathological changes in the central nervous system, liver, kidneys and skeletal muscles observed in some hyperhomocysteinemia patients have been attributed to a direct cytotoxic effect exerted by homocysteine.

In addition to the adverse effects attributed to homocysteine, other sulfur-containing amino acids, such as cysteine, have also been associated with vascular and connective tissue disorders. It has recently been appreciated that abnormalities in the oxidative metabolism of cysteine are found in rheumatoid arthritis and systemic lupus. These disease states are also associated with vasculitis (Gordan et al., Lancet 339:25–26 (1992)).

Currently available methods for treating hyperhomocysteinemia consist essentially of administration of vitamin supplements, such as pyridoxine, folate, choline, betaine, or cobalamin, in an attempt to reduce serum homocysteine levels. A few afflicted infants, diagnosed in the newborn period, have been treated successfully with methionine-restricted, cystine-supplemented diets. However, the success of this method depends on accurate diagnosis within the newborn period, and accounts for a very small number of those patients afflicted with hyperhomocysteinemia.

Vitamin therapy has been shown to cause a decrease in plasma homocysteine levels in some patients; however, numerous patients afflicted with hyperhomocysteinemia experience little or no reduction in homocysteine levels as a result of this therapy. Furthermore, vitamin therapy does not directly counteract the toxic effects of homocysteine, or provide a means to ameliorate the pathological effects resulting from past exposure to homocysteine. Consequently, there is no evidence that current modes of therapy reduce the risk of atherothrombotic (or other) complications in afflicted adults.

Successful treatment of hyperhomocysteinemia depends, not only on the immediate reduction of homocysteine levels, but more importantly, on directly counteracting the toxic effect produced by homocysteine. Therefore, a clinical need exists for a pharmacological method which directly counteracts the immediate toxicity of homocysteine and also ameliorates the pathophysiological abnormalities resulting from past exposure to homocysteine.

SUMMARY OF THE INVENTION

The invention relates to a method for the treatment or prevention of disease states associated with elevated levels of homocysteine, comprising administering a therapeutically effective amount of a nitrosating compound to a patient in need thereof. In particular, the nitrosating compound may be selected from the group of NO donors consisting of nitroglycerin, S-nitrosothiols, S-nitroso-proteins, nitric oxide, nitroprusside, thionitrites, thionitrates, iron-nitrosyl compounds, sydnonimines, furoxans, nitrosonium salts, and related compounds.

The invention also relates to the method of the invention, wherein the S-nitrosothiol compound is selected from the group consisting of S-nitroso-N-acetylcysteine, S-nitroso-glutathione, S-nitroso-cysteine, S-nitroso-homocysteine, S-nitroso-pantathoeine derivatives, S-nitroso-penicillamine, S-nitroso-captopril, long-chain lipophilic nitrosothiols, and s-nitrosodithiols.

The invention also relates to the method of the invention, wherein the nitrosating compound is administered as part of a pharmaceutical composition comprising a pharmaceutically acceptable carrier.

The invention further relates to a method wherein said pharmaceutical composition is administered to a patient by a route comprising oral, sublingual, intravenous, intramuscular, or aerosol delivery.

The invention also relates to the method of the invention, wherein said disease state is a vascular disorder selected from the group consisting of coronary occlusion, atherosclerosis, venous thrombosis, arterial thrombosis, renovascular hypertension, intermittent claudication, mesenteric ischemia, cerebrovascular incidents, and pulmonary embolism.

The invention also relates to the method of the invention, wherein the disease state is a connective tissue disorder selected from the group consisting of ectopia lentis, mental retardation, developmental retardation, psychomotor dysfunction, skeletal deformities and osteoporosis.

The invention also relates to the method of the invention, wherein the disease state comprises homocysteine-induced cytotoxicity.

The invention also relates to a method for the treatment or prevention of disease state resulting from elevated levels of sulfur-containing amino acids, comprising administering a therapeutically effective amount of a nitrosating compound to a patient in need thereof.

The invention also relates to the method of the invention wherein said amino acid is selected from the group consisting of homocysteine, cysteine, cystine and methionine.

The invention also relates to the method of the invention wherein said disease state comprises a vascular disorder, cytotoxicity, or connective tissue disorder.

DESCRIPTION OF THE FIGURES

Various other objects, features, and attendant advantages of the present invention will be more fully appreciated as the same becomes more readily understood when considered in conjunction with the accompanying Figures.

A: Ultraviolet absorption spectrum.
B: [$^{15}$N]-NMR spectrum.

C: Loss of homocysteine peak and replacement with peak of slower electrophoretic mobility.

D: S-nitroso-homocysteine peak.

E: Homocysteine thiolactone peak.

Figure 2:
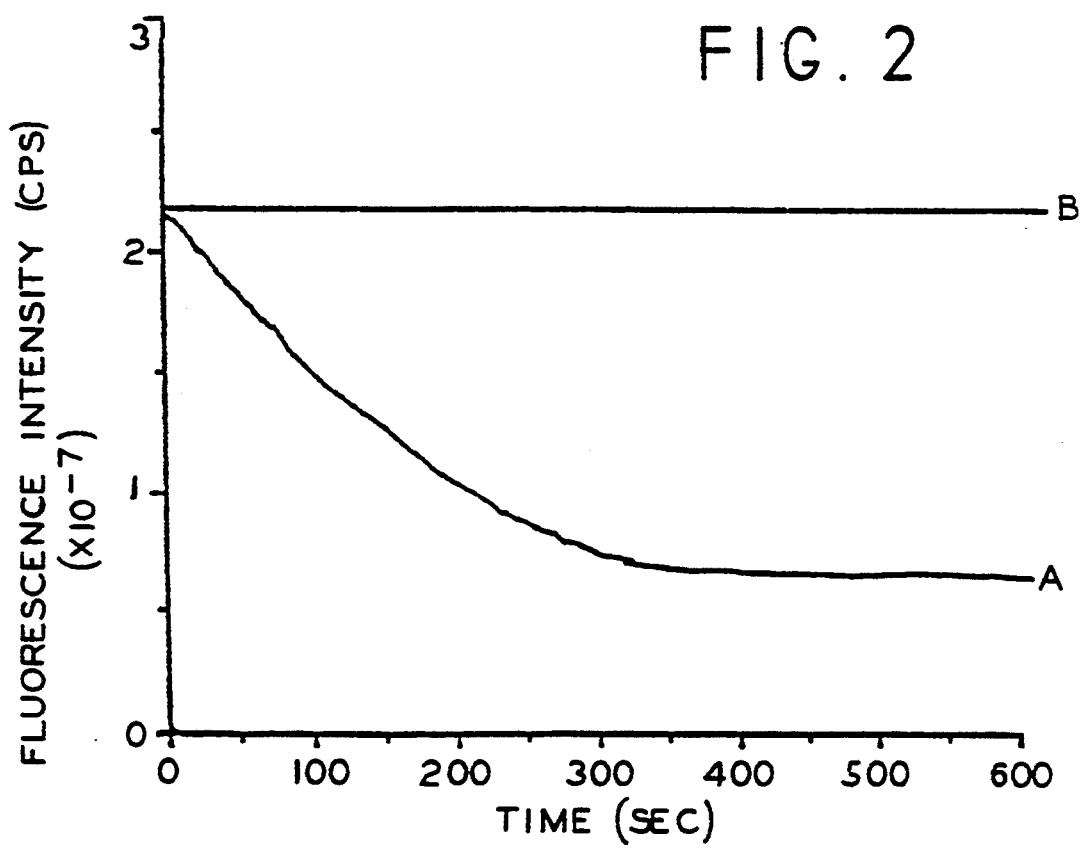

FIG. 2: Homocysteine-mediated-$H_2O_2$ generation, and prevention of $H_2O_2$ generation by nitrosation.

Figure 3A:
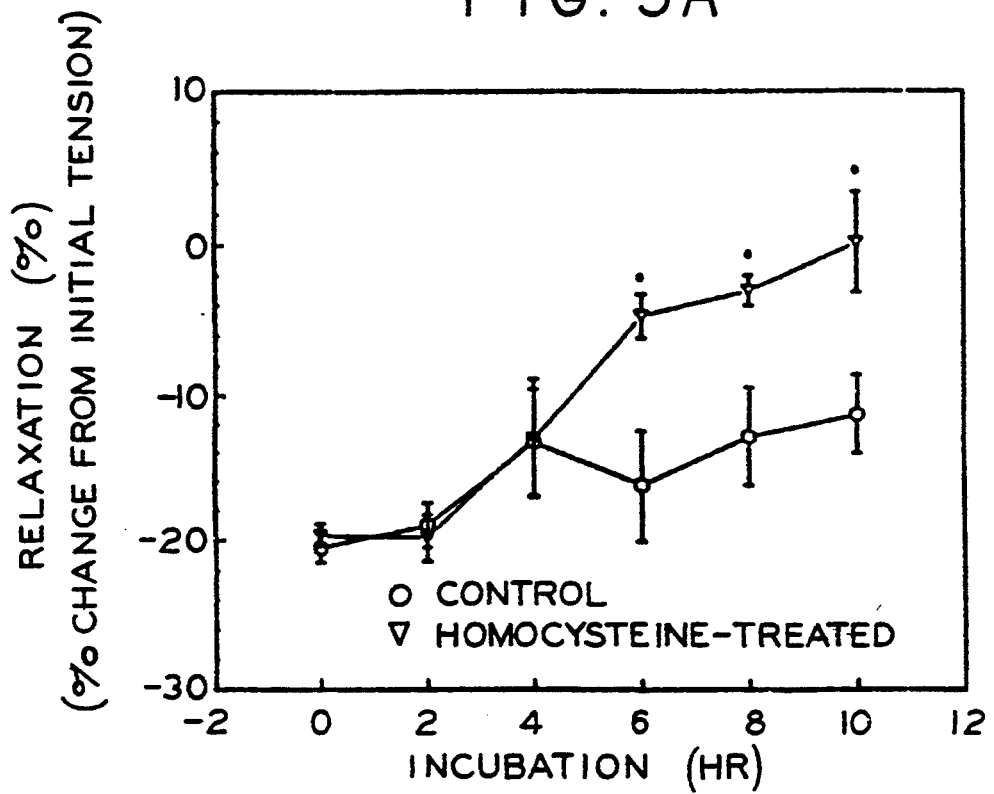
Figure 3B:
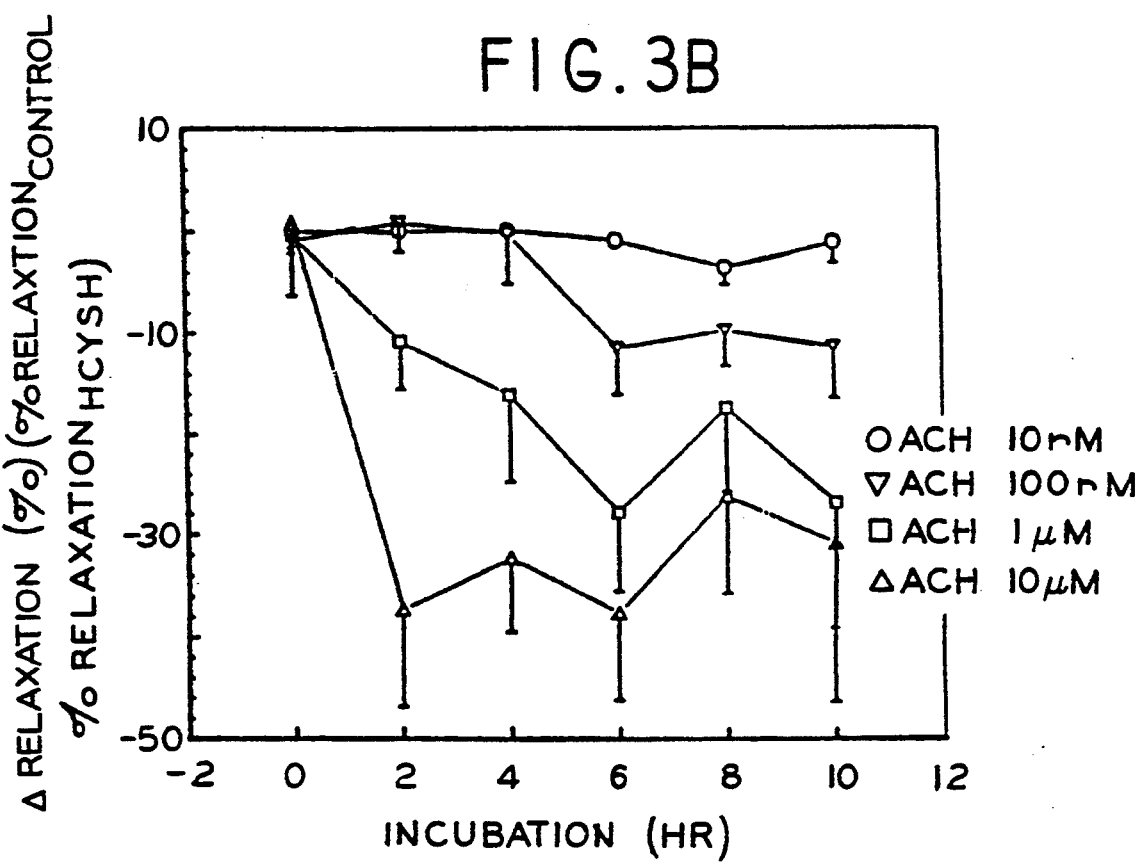

FIG. 3: Homocysteine-induced endothelial dysfunction.

A: Endothelium-dependent relaxations induced with acetylcholine (O) control, and homocysteine (▽).

B: Relaxations of homocysteine-exposed vessels to acetylcholine.

Figure 4:
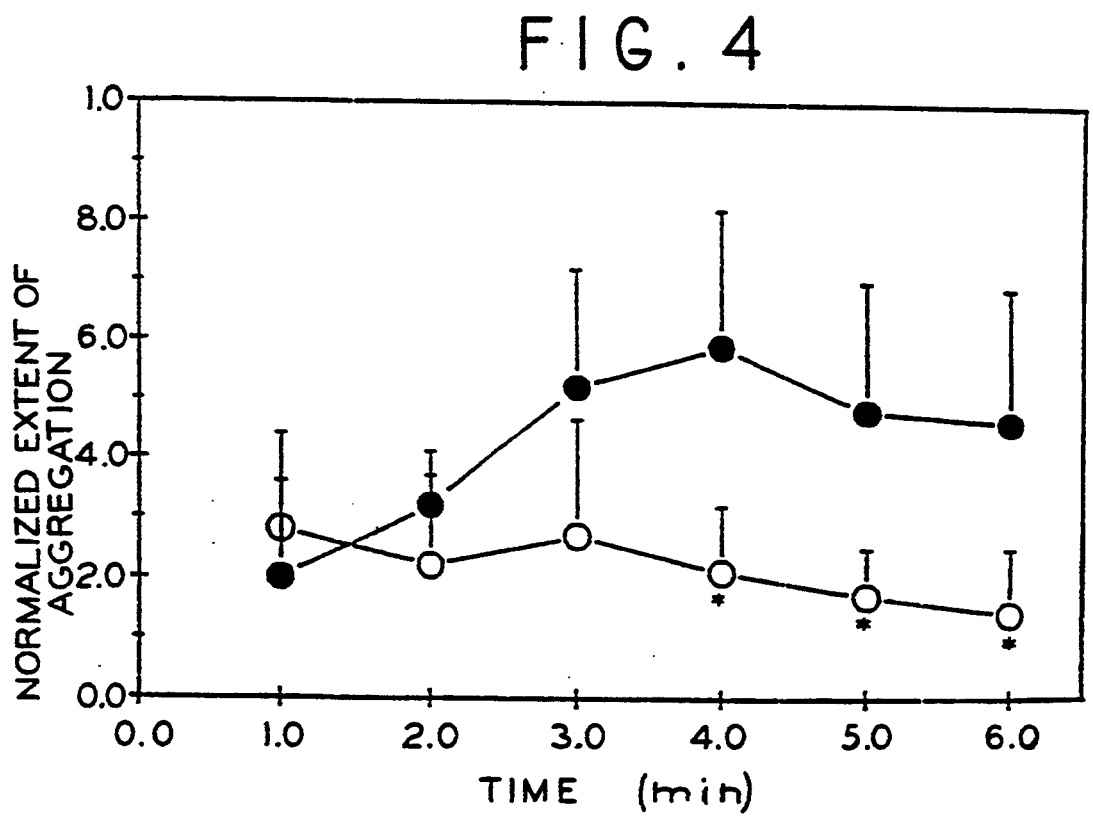

FIG. 4: Homocysteine-mediated attenuation of platelet inhibition by EDRF shown in endothelial cells incubated in the presence (●) or absence (O) of homocysteine.

Figure 5A:
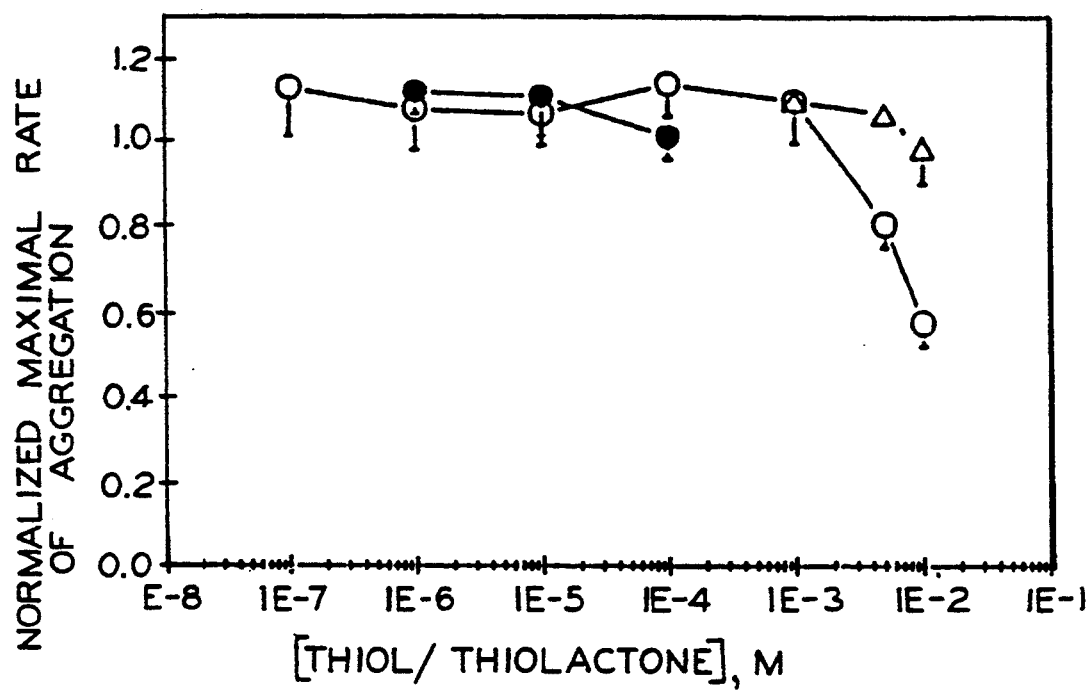
Figure 5B:
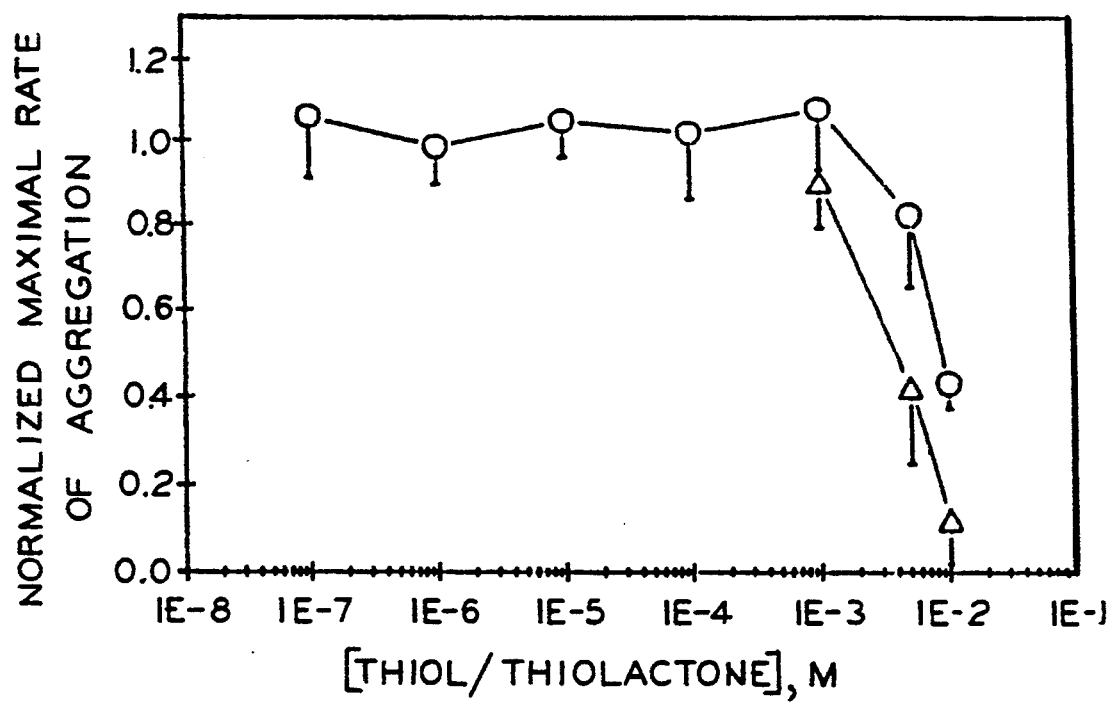

FIG. 5: Dose-effect curves for platelet inhibition by homocysteine (O), HTL (free base) (Δ), and HTL (hydrochloride) (▲), plotted as maximal rate of aggregation relative to control.

Aggregation in PRP induced with 15 uM ADP.

B: Aggregation in PRP induced with 0.16 mg/ml collagen.

Figure 6A:
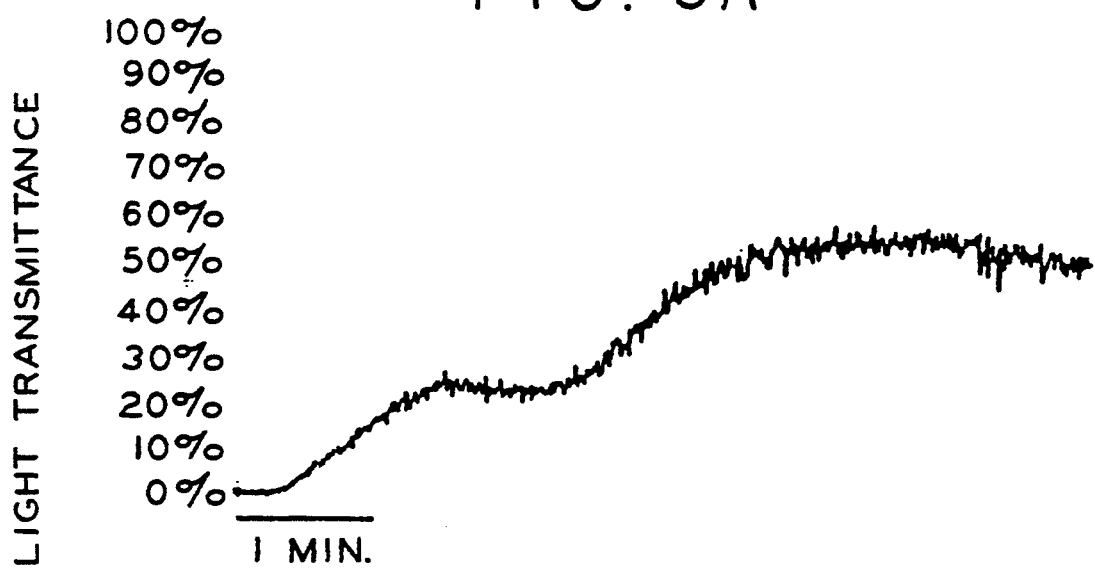
Figure 6B:
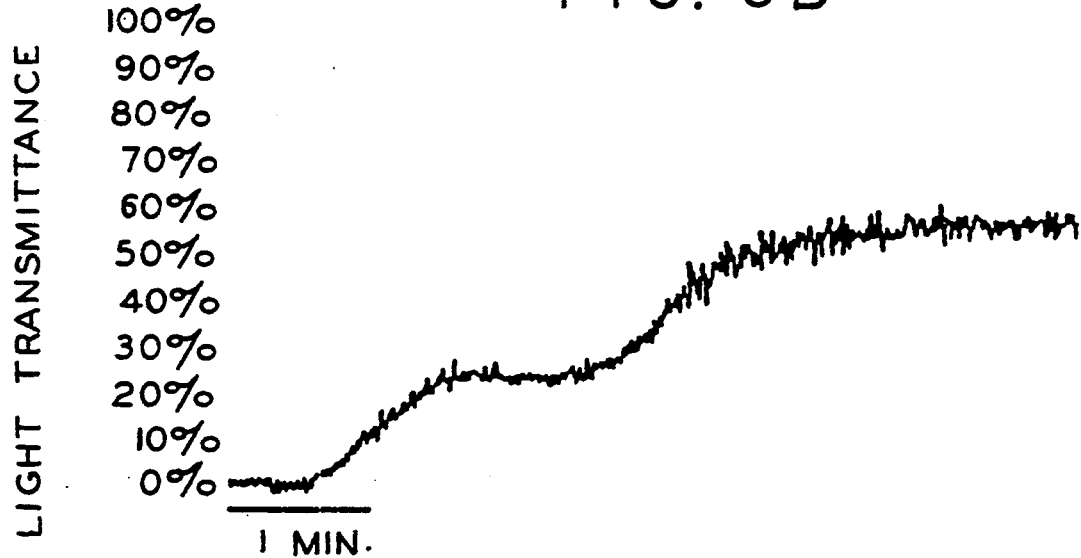

FIG. 6: Platelet aggregation caused by HTL.

A: Aggregation induced by 2 ul of HTL (free base) extracted into chloroform.

B: Aggregation induced by 2 ul of HPLC grade chloroform solvent.

Figure 7:
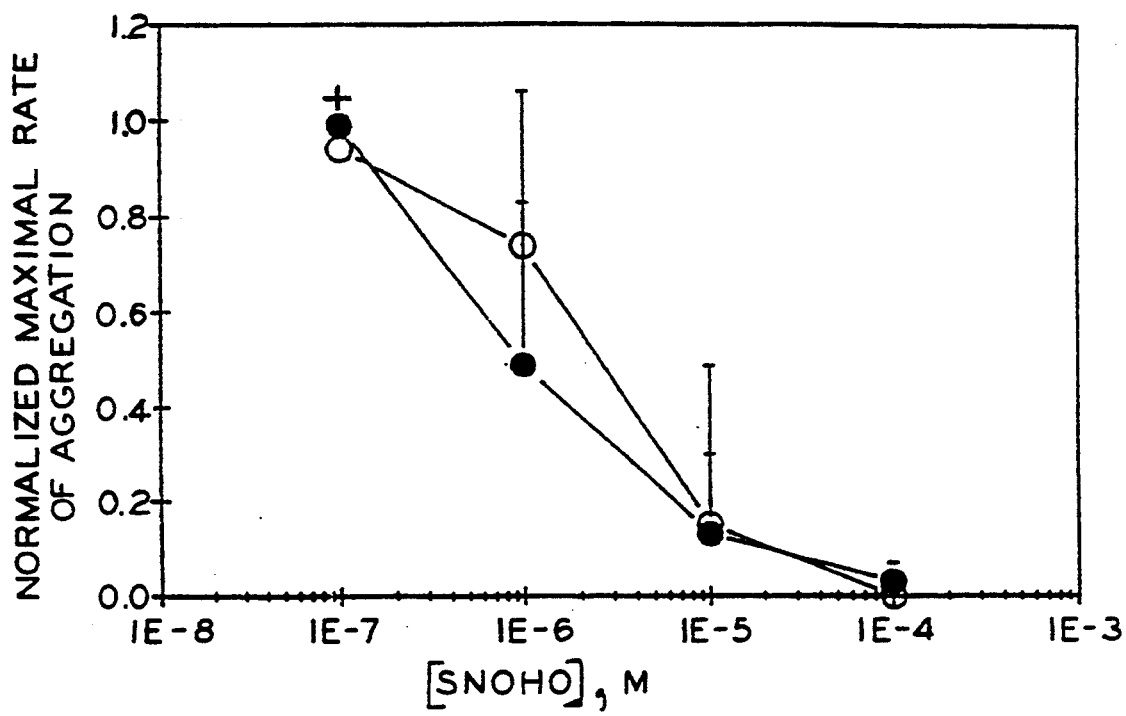

FIG. 7: Dose-dependent inhibition by S-nitroso-homocysteine, of platelet aggregation induced by ADP (O) and collagen (●).

Figure 8:
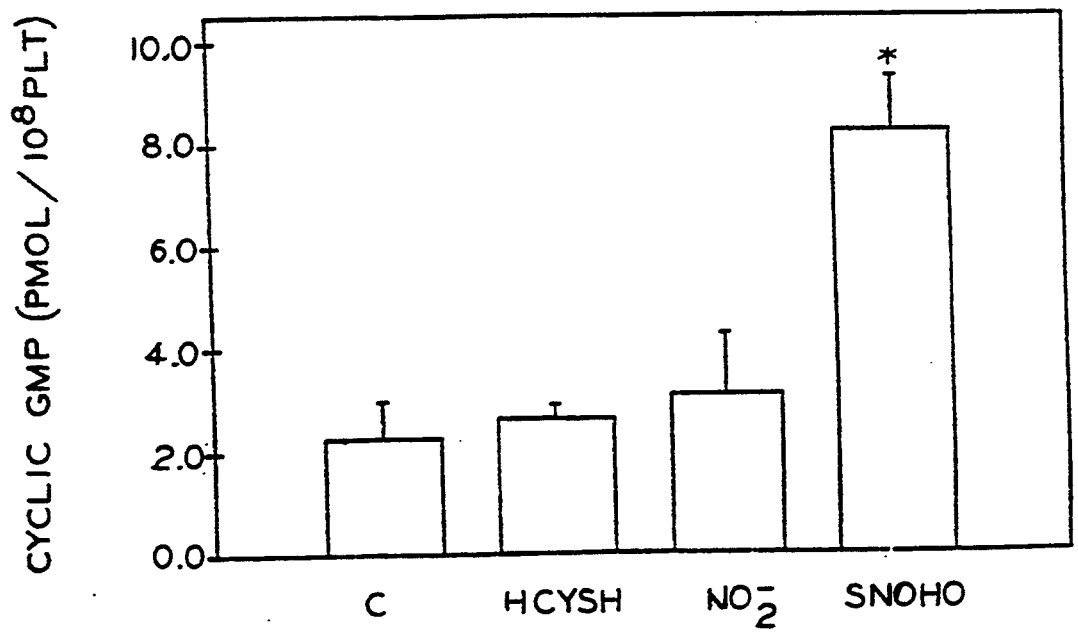

FIG. 8: Platelet cyclic GMP production by S-nitroso-homocysteine.

FIG. 9: Detection of S-nitroso-homocysteine formation from endogenous oxides of nitrogen.

A: In the presence of 1 mM homocysteine.

B: Paired sample of (a) after treatment with HgCl2.

C: In the absence of 1 mM homocysteine.

D: Paired sample of (c) after treatment with HgCl2.

FIG. 10: Platelet inhibition by S-nitroso-homocysteine.

A: Relative to control aggregation (a) and homocysteine, exposed to unstimulated endothelial cells (b).

B: Dose-effect relationship for inhibition by S-nitroso-homocysteine synthesized from NaNO2 (●) and EDRF (O).

Figure 11:
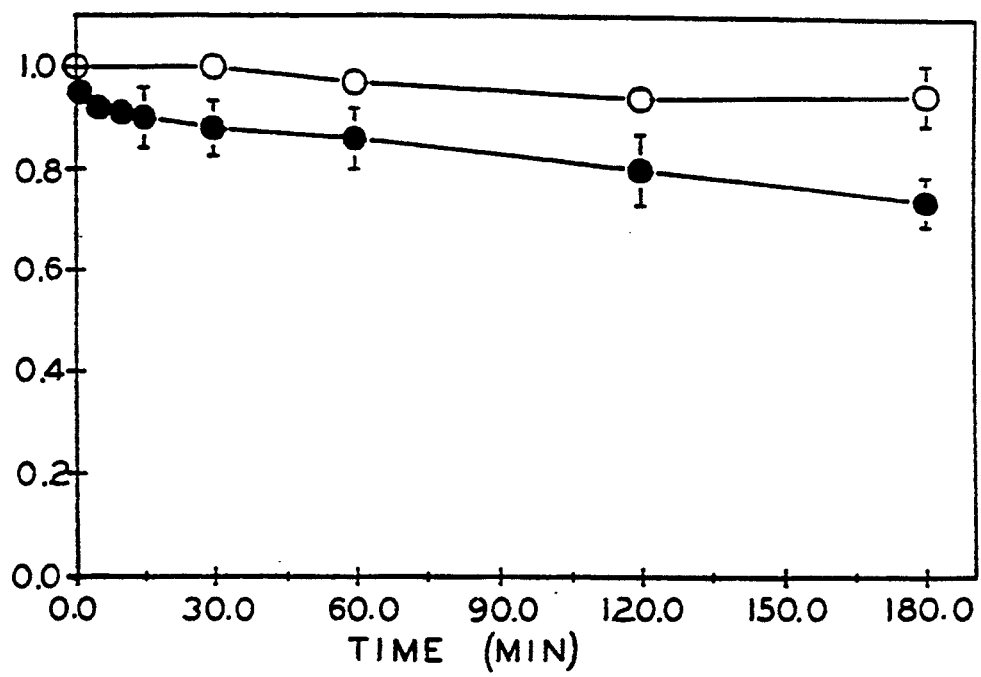

FIG. 11: Stability of S-nitroso-homocysteine, at pH 7.4 (●) and p.H 2.5 (O).

Figure 12:
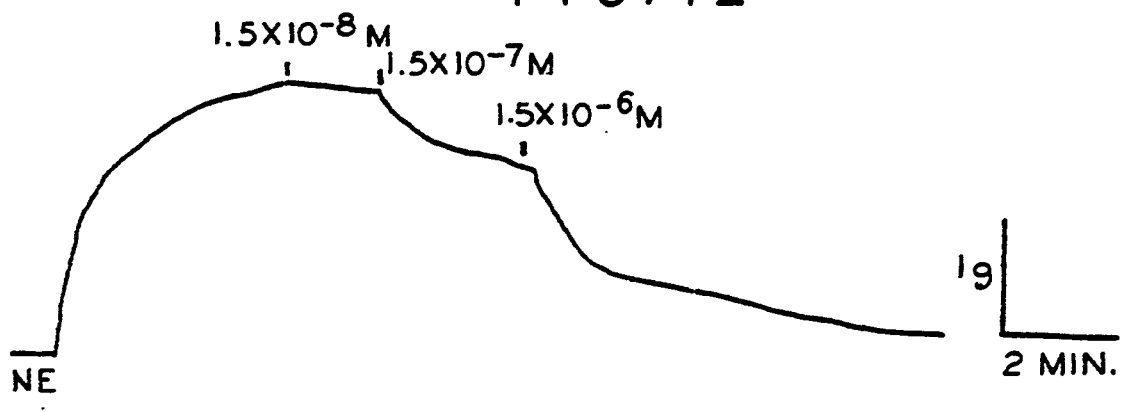

FIG. 12: S-nitroso-homocysteine induced vasorelaxation.

Figure 13:
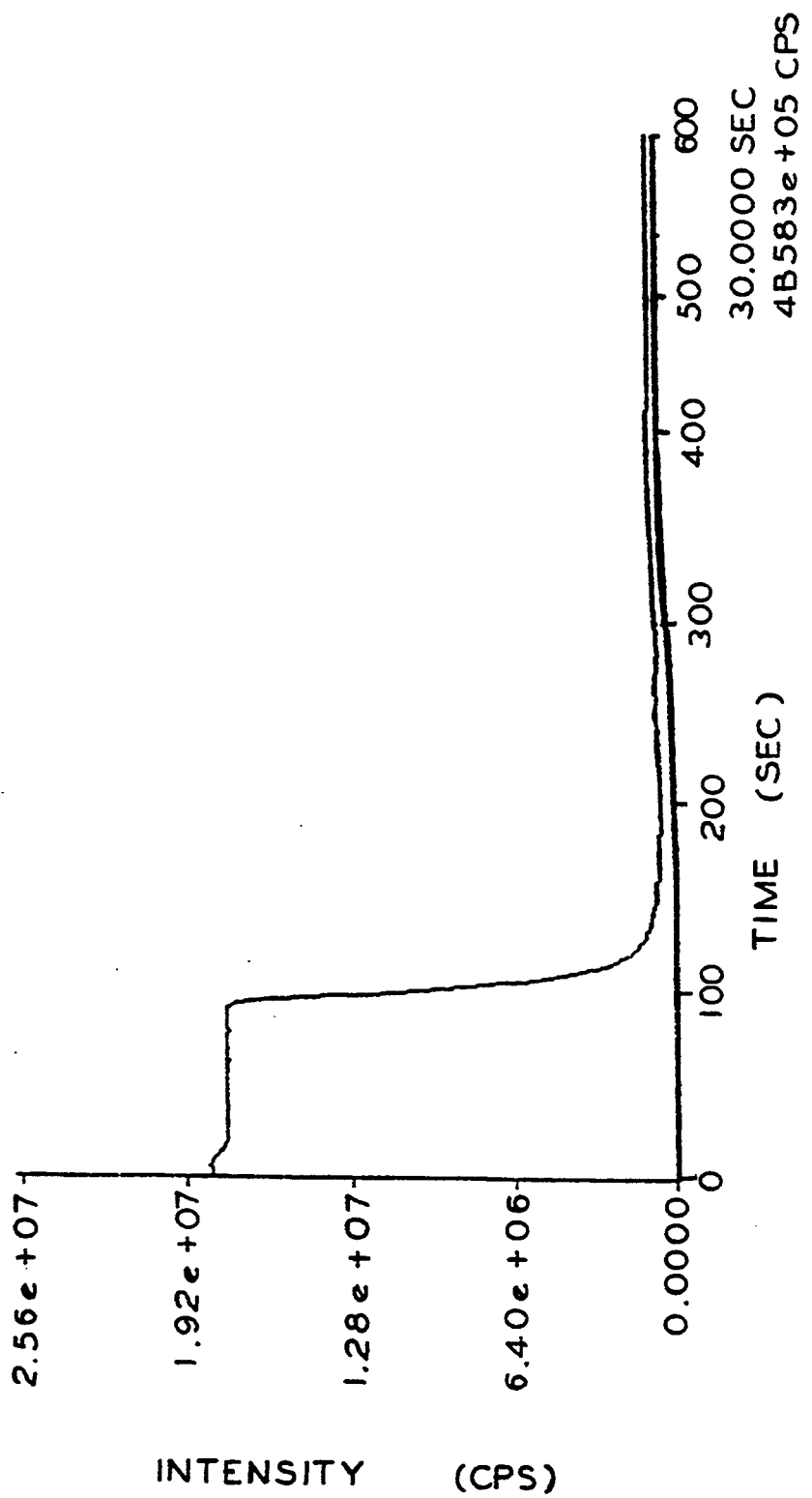

FIG. 13: $H_2O_2$ generation by cysteine.

Figure 14:
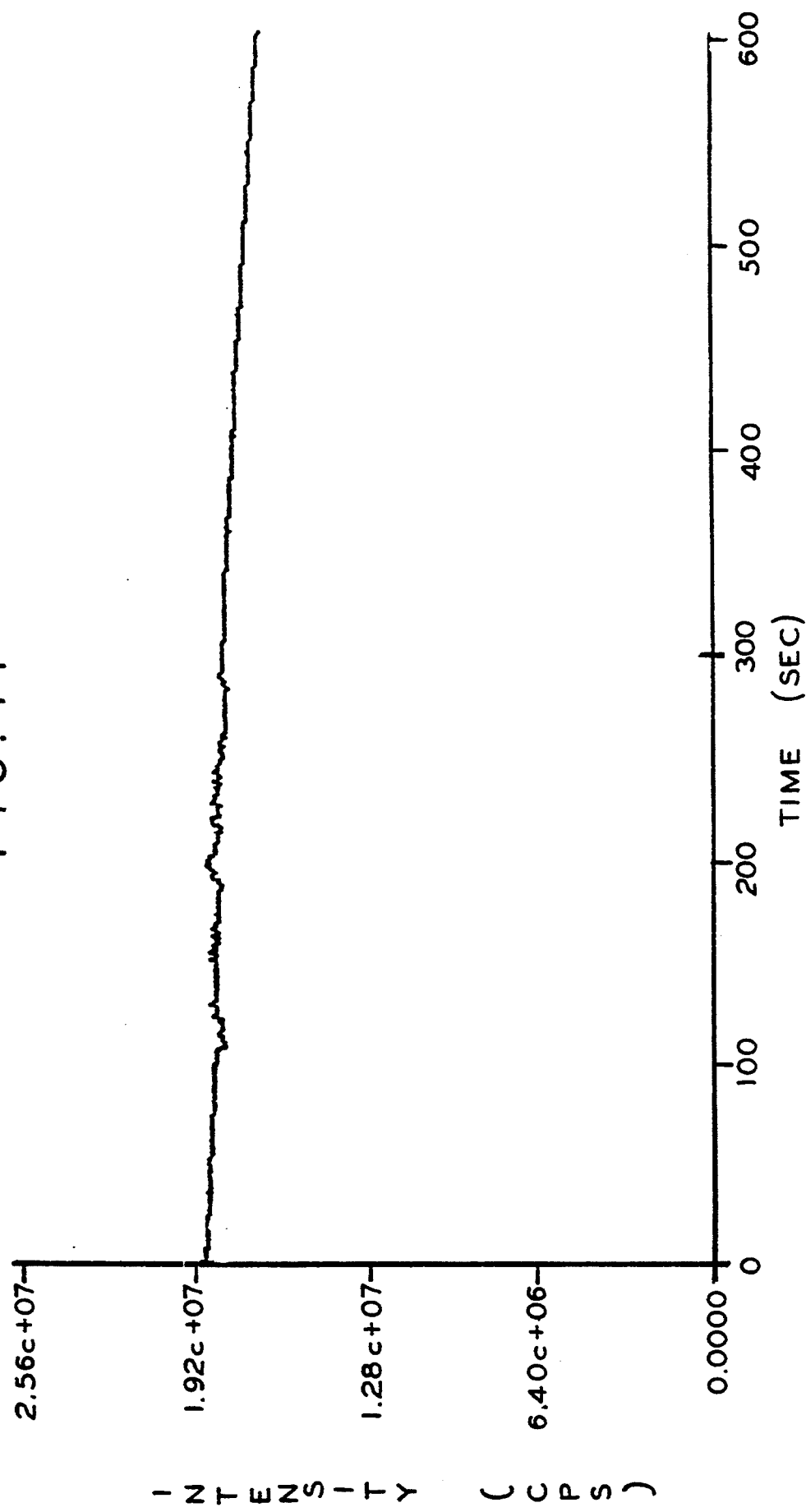

FIG. 14: Blockade of $H_2O_2$ generation of cysteine, by S-nitrosation.

Figure 15:
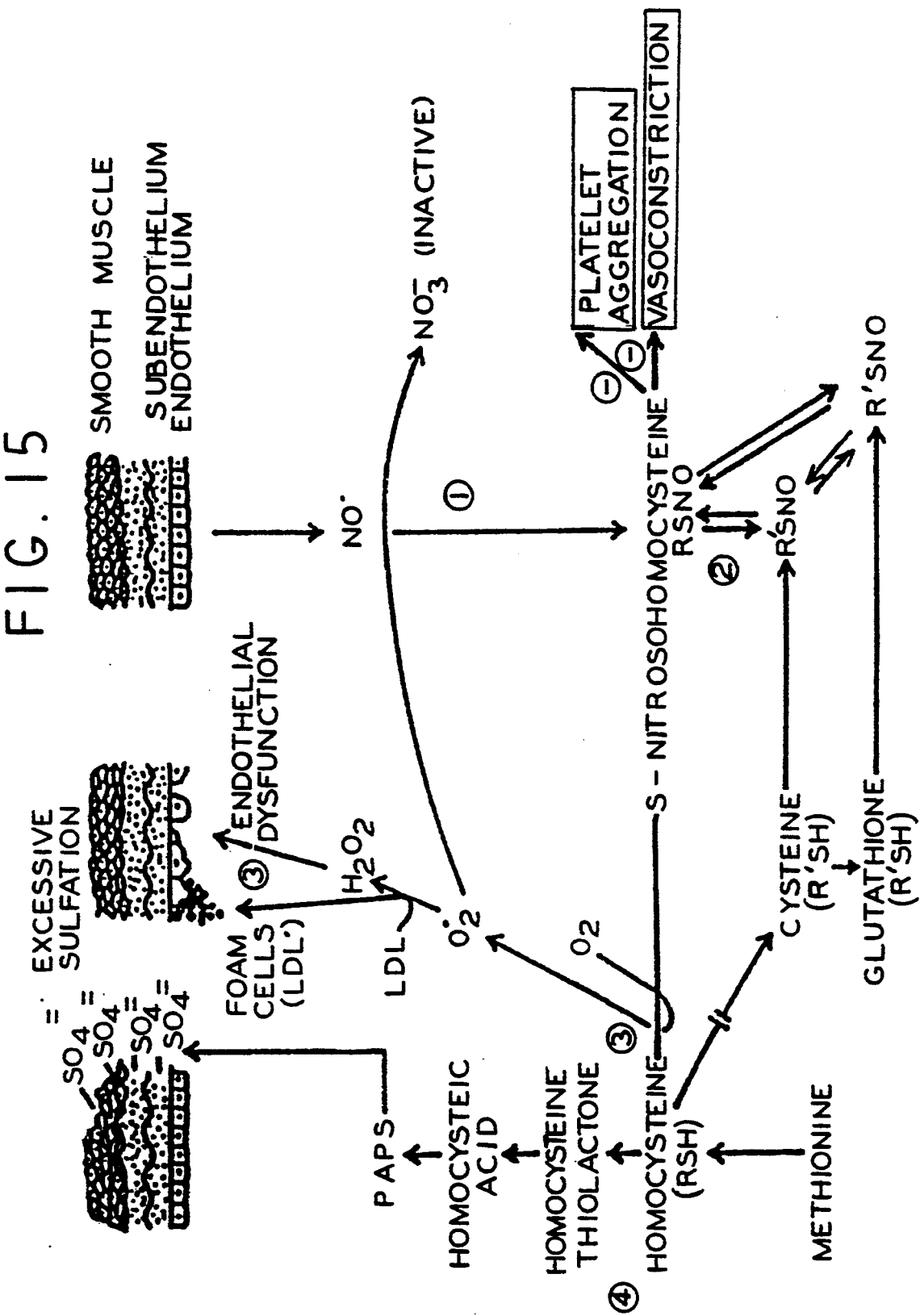

FIG. 15: Proposed mechanism of homocysteine-mediated atherothrombosis and its modulation by NO.

DESCRIPTION OF THE PREFERRED EMBODIMENTS

The invention is related to the discovery that administration of a nitrosating compound to a patient may be used to treat or prevent pathophysiological conditions associated with hyperhomocysteineimia. Such disorders include vascular, neurological, ocular and skeletal complications resulting from hyperhomocysteineimia. The term "nitrosating compound" refers to a compound capable of delivering NO in vivo. Typical nitrosating compounds include nitroglycerin, S-nitrosothiols, nitric oxide, S-nitroso-proteins, nitroprusside, and related compounds. Typical compounds to which the term "S-nitrosothiol" refers include, but are not limited to S-nitroso-N-acetylcysteine, S-nitroso-glutathione, S-nitrosocysteine, S-nitrosohomocysteine, S-nitroso-pantathoeine derivatives, S-nitroso-penicillamine, S-nitroso-captopril, long-chain lipophilic nitrosothiols, and S-nitrosodithiols.

One embodiment of the invention relates to the administration of a nitrosating compound to treat or prevent vascular disorders associated with hyperhomocysteinemia. In particular, such vascular disorders include, but are not limited to, atherosclerosis, venous thrombosis, arterial thrombosis, coronary occlusion, renovascular hypertension, intermittent claudication, mesenteric ischemia, cerebrovascular incidents, and pulmonary embolism.

As demonstrated by the inventors, hyperhomocysteinemia promotes atherosclerosis and thrombosis through endothelial injury, mediated largely by $H_2O_2$ generated from the SH group of homocysteine. The endothelial injury results in a deficiency of NO normally required to counteract platelet aggregation and vasoconstriction.

Administration of a nitrosating compound to a patient directly counteracts the thrombogenic and atherogenic effects of homocysteine in a number of ways which include, but are not limited to, the following mechanisms. Nitrosation of homocysteine prevents $H_2O_2$ generation from the SH groups, as well as the oxidative conversion of homocysteine to HTL, and thus, prevents homocysteine-induced endothelial injury. In addition, the nitrosating compound delivers NO in vivo, which corrects the NO deficiency caused by thiol-induced endothelial injury. This NO then reacts to form S-nitrosothiols which counteract thrombogenesis by exerting potent vasodilatory and platelet-inhibitory effects.

Another embodiment of the invention relates to the administration of a nitrosating agent to treat or prevent connective tissue disorders associated with hyperhomocysteinemia. The term "connective tissue" refers to the extracellular components which provide structural support to the body and bind together its cells, organs, and tissues. The major connective tissues are bone, skin, tendons, ligaments and cartilage; however, the term is also applied to blood vessels, synovial spaces, fluids, membranes and septa. Examples of particular connective tissue disorders include, but are not limited to, vascular fibrosis, ectopia lentis, osteoporosis, skeletal abnormalities, rheumatoid arthritis, systemic lupus, mental retardation, and delayed psychomotor development.

Another embodiment of the invention relates to the administration of a nitrosating compound to treat or prevent the cytotoxic effect exerted by homocysteine. The term "cytotoxic" means that which is detrimental or destructive to cells, or interferes with normal cellular function. The cytotoxic effect of homocysteine may be exerted upon the cells of any organ system including, but not limited to, liver, kidney, heart, blood vessel and brain.

A particular embodiment of the invention involves the use of lipophilic nitrosothiols to provide delivery of NO to the brain. Because of their lipophilic nature, these compounds have the ability to penetrate the blood-brain barrier, thus achieving direct access to the central nervous system. Administration of these compounds provides a means for direct and local elimination of the toxic effects exerted by homocysteine on the central nervous system.

Another embodiment of the invention relates to the administration of a nitrosating agent to treat or prevent disease states associated with other sulfur-containing amino acids. Such amino acids include cysteine, cystine and methionine. The disease states associated with these amino acids include, but are not limited to atherosclerosis, thrombosis, cytotoxicity, connective tissue disorders, rheumatoid arthritis, systemic lupus and associated vasculitis.

The inventors have demonstrated that the SH group of cysteine generates $H_2O_2$. As with homocysteine, $H_2O_2$ mediates the endothelial injury which leads to the atherogenic and thrombotic effects of cysteine. S-nitrosation of cysteine blocks $H_2O_2$ generation, and thus, provides a means for attenuating the thiol-induced toxicity of cysteine.

In addition to nitrosating agents, the SH group of homocysteine can be blocked by other chemical means. For example, SH blockage can be accomplished by disulfide formation, achieved by administration of a thiol. Suitable thiols include, but are not limited to, N-acetylcysteine, glutathione, and captopril. Thus, thiol administration provides an additional means for attenuating the toxic effects exerted by the SH group of homocysteine and other sulfur-containing amino acids.

An additional embodiment of the invention relates to the administration of an S-nitrosothiol compound as part of a pharmaceutical composition, comprising a pharmaceutically acceptable carrier, to achieve the physiological effects discussed above.

The pharmaceutical compositions utilized in this invention can be administered by intranasal, oral, enteral, topical, sublingual, rectal, intramuscular, intravenous, or subcutaneous means.

The compounds of this invention can be employed in combination with conventional excipients; i.e., pharmaceutically acceptable organic or inorganic carrier substances suitable for parenteral, enteral or intranasal application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable vehicles consist of solutions, preferably oily or aqueous solutions, as well as suspensions, emulsions, or implants, including suppositories. Ampules are convenient unit dosages.

The pharmaceutical compositions utilized in this invention can be administered by intranasal, oral, enteral, topical, sublingual, rectal, intramuscular, intravenous, or subcutaneous means.

For enteral application, particularly suitable are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

It will be appreciated that the actually preferred amounts of active compounds used will vary according to the specific compound being utilized, the particular compositions formulated, the mode of application and the particular site of administration. Optimal administration rates for a given protocol of administration can be readily ascertained by those skilled in the art, using conventional dosage determination tests conducted with regard to the foregoing guidelines.

According to the present invention, a "therapeutically effective amount" of a pharmaceutical composition is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect.

Without further elaboration, it is believed that one skilled in the art can, using the preceding description, utilize the present invention to its fullest extent. The following examples are, therefore, to be construed as merely illustrative, and not limitative of the remainder of the disclosure in any way whatsoever.

The entire text of all publications cited above and below are hereby incorporated by reference.

EXAMPLES

Materials

Homocysteine, homocystine, HTL (free base and hydrochloride), homocysteic acid, cupric sulfate, ferrous sulfate, methylene blue, sepharose 2B-300, acetylsalicylic acid, epinephrine, ADP, acetylcholine, and calcium ionophore A23187 were purchased from Sigma Chemical Co. (St. Louis, Mo.). Bovine thrombin was obtained from ICN, ImmunoBiologicals (Lisle, Ill.). Sulfanilamide and N-(1-naphthyl)ethylenediamine dihydrochloride were purchased from Aldrich Chemical Co. (Milwaukee, Wis.). Calf skin collagen was obtained from Worthington Biochemical (Freehold, N.J.). Sodium nitrite was purchased from Fisher Scientific (Fairlawn, N.J.). NO gas was purchased from Matheson Gas Products. Radioimmunoassay kits for the determination of cyclic GMP levels were purchased from New England Nuclear (Boston, Mass.). Hepes buffered saline (HBS) consisted of 140 mM NaCl, 6 mM HCl, 6 mM N-[2-hyroxyethyl]-piperazine-N-[2-ethane-sulfinic acid], 2 mM $NA_2HPO_4$, 2 mM $MgSO_4$, 0.1% dextrose and 0.4% bovine serum albumin. Phosphate buffered saline (PBS) consisted of 140 mM NaCl, 10 mM sodium phosphate, pH 7.4. Kreb's buffer consisted of 140 mM NaCl, 4.7 mM KCl, 2.5 mM $CaCl_2$, 1.2 mM $MgSO_4$, 1.2 mM $KH_2PO_4$, 12.5 mM $NaHCO_3$, and 11 mM D-glucose.

EXAMPLE 1:

The Oxidative Metabolism of Homocysteine and It's Reactivity Towards Oxides of Nitrogen a. Analytical Chemical Methods The chemical method of Saville was used for detection of S-nitrosothiols (Saville, Analyst 83:670-672 (1958)). The method, which assays free $NO_x$ in solution, involves a diazotization reaction with sulfanilamide and subsequent coupling with the chromophore N-(1-naphthyl)ethylenediamine. The specificity for S-nitrosothiols derives from assay determinations performed in the presence and absence of $HgCl_2$, the latter reagent catalyzing the hydrolysis of the S-NO bond (Saville, Analyst 83:670-672 (1958)).

The determination of S-nitrosothiol absorption was performed using a Gilford Response UV/VIS spectrophotometer. Nuclear magnetic resonance-measurements of RS-NOs were made according to the method of Bonnett and colleagues (Bonnett et al., JCS Perkins Trans. I:2261-2264 (1975)). [$^{15}$N]NMR spectra were recorded with a Brucker 500 MHZ spectrometer, Billerica, Mass. Deuterium lock was effected with $[D]_2O$ and the spectra referenced to an [$^{15}$N] natural abundance spectrum of a saturated solution of $NaNO_2$ at 587 ppm. Spectra were recorded at 50.68 MHZ and the nine transients of 16K data points collected with a 30°-pulse width and a 10-second relaxation delay. Data were multiplied by a 2-Hz exponential line broadening factor before Fourier transformation.

Chemiluminescence analyzers operate on the principal that the reaction of NO with ozone results in the emission of detectable light. The major limitation of standard methodology as it pertains to biological analyses is the inability to distinguish NO free in solution and that derived from $NO_x$ and s-nitrosothiols (Palmer et al., Nature 327:524-526 (1987)). This lack of specificity derives in large part from the requirement of a reducing reflux chamber for sensitive detection of NO. Therefore, we adapted a highly sensitive new analyzer (TEA model 543, Theremedics, Inc.) for the purpose of specific S-nitrosothiol detection. This instrument utilizes UV photolysis to cleave NO from parent nitroso-compounds, in place of chemical reduction.

This method, however, is notably ineffective at cleaving NO from $NO_x$ (for which catalytic pyrolysis is employed). Thus, nitroso-compounds are readily identified and distinguished from authentic NO by requisite UV photolysis for signal detection. S-nitrosothiols are further distinguished from other nitroso-compounds by sample pretreatment with excess $HgCl_2$ under aerobic atmospheric conditions for five minutes. By binding to SH groups selectively, NO is displaced from S-nitrosothiols (Saville, Analyst 83:670-672 (1958)) and rapidly autooxidizes to higher forms of nitrogen ($NO_x$), for which the sensitivity of detection is extremely poor. Accordingly, S-nitrosothiols are identified by: 1) The requirement of UV photolysis for detection of signal, and 2) the successful elimination of signal by sample pretreatment with $HgCl_2$. The sensitivity of this method for S-nitroso-homocysteine detection approaches 1 pM and the reproducibility is within 2%. These values are within ranges reported for the detection of other nitroso-compounds with this analyzer.

Chemical methods for separating homocysteine from its various oxidized and S-nitrosated derivatives are not available. The following electrophoretic method was developed for this purpose.

Isotachophoretic analyses were performed on the BioRad HPE-100 capillary system (BioRad, Richmond, Calif.), fitted with a silica-coated capillary (20 cm × 25 cm). Electrophoretic separations were detected on-line and recorded with a model 1321 single pen strip chart recorder (BioRad, Richmond, Calif.) programmed at a chart speed of 1.0 cm/min with a rise time of one second. Samples were injected using Hamilton syringes and analyses performed at room temperatures.

To initiate analyses, the capillary and electrode reservoirs were filled with electrophoresis buffer (0.1M phosphate, pH 2.5), and the polarity of the internal power supply was set for the migration of cations towards the detector (+ polarity). The inlet was then flushed with deionized water and a 10 ul sample, diluted in 0.01N HCl, 0.01M sodium phosphate (pH 2.3) was loaded for nine seconds at 11 kV. The inlet electrode reservoir was subsequently flushed with electrophoresis buffer and the sample run performed at 11 kV. Between analyses, the capillary was also flushed with separation buffer. Eluted volumes were monitored at 200 nm for optimal sensitivity. Confirmatory evidence for S-nitrosothiol detection was obtained at 320 nm (Myers et al., Nature 345:161-163 (1990)).

b. Synthesis and Chemical Characterization of S-nitroso-homocysteine

S-nitroso-homocysteine was prepared by a standard method of nitrosation, in which homocysteine was treated with an equivalent of acidified $NaNO_2$ (0.5N HCl) at 25° C. (Kowaluk et al., J. Pharmacol. Exp. Ther. 256:1256-1264 (1990); Aldred et at, J. Chem. Soc. Perking Trans. II:777-782 (1987); Byler et at, J. Agric. Food Chem. 31:523-527 (1983)).

Figure 1A:
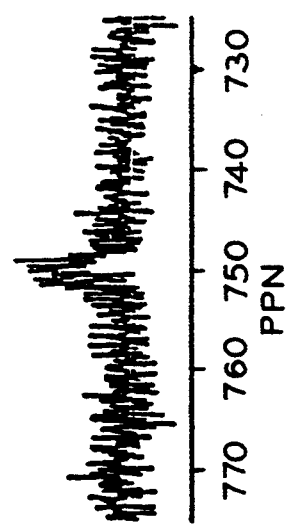
FIG. 1: Spectroscopy and chemical characterization of S-nitroso-homocysteine.
Figure 1B:
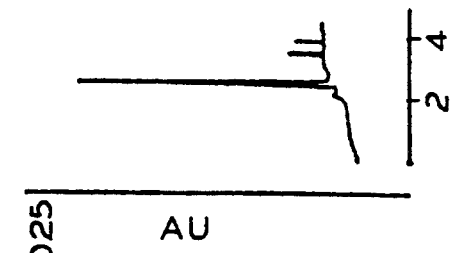

Under these conditions. the general reaction of thiol with oxide of nitrogen is reported to be complete and stoichiometric For homocysteine, however, the acid catalyzed conversion to a lactone derivative (Riegel et at, J. Biol. Chem. 112:149-154 (1935)) is a potential competing reaction that requires examination. Characteristic of other S-nitrosothiols, the above solutions turned red rapidly upon product formation, and displayed distinct absorption maxima at approximately 250 nm, 340 nm and 550 nm, as shown in FIG. 1A. The calculated absorbtivity of this compound at 547 nm is 16.7 $cm^{-1}$, and which correlates well with the published values of 16.6 and 16.1 for S-nitroso-cysteine and S-nitroso-glutathione, respectively (Kowaluk et at, J. Pharmacol. Exp. Ther. 256:1256-1264 (1990)). Using [$^{15}$N]-NMR solutions of homocysteine treated with acidified Na[$^{15}$N]$O_2$ exhibited a chemical shift at 750 ppm relative to an internal [$^{15}$N] standard, indicative of S-NO bond formation, as shown in FIG. 1B.

Figure 1C:
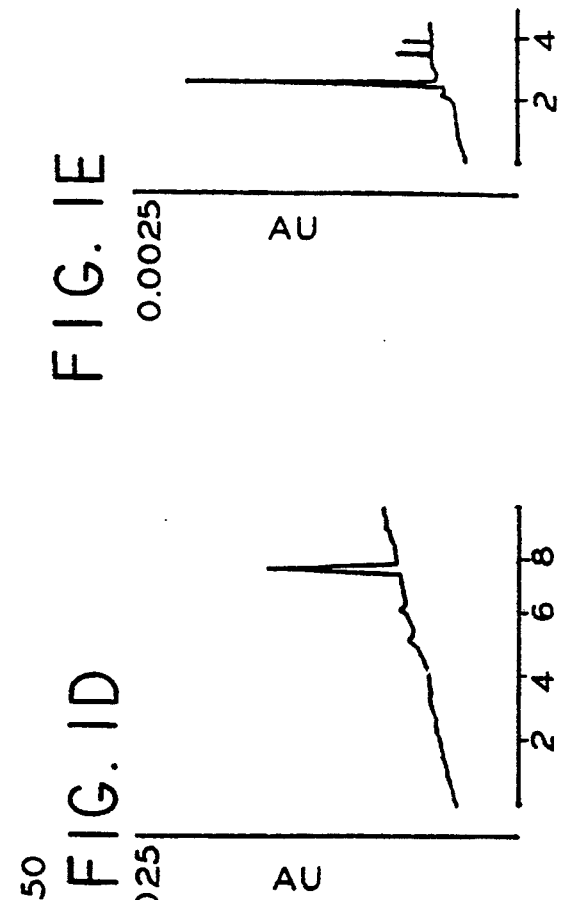
Figure 1D:
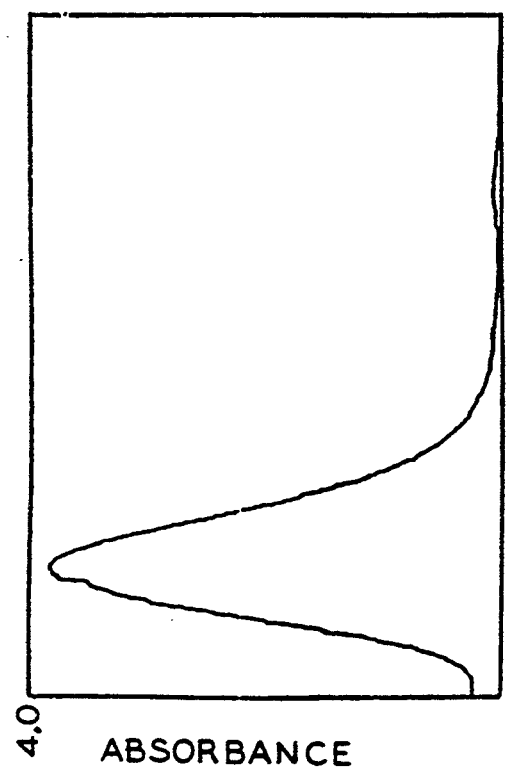
Figure 1E:
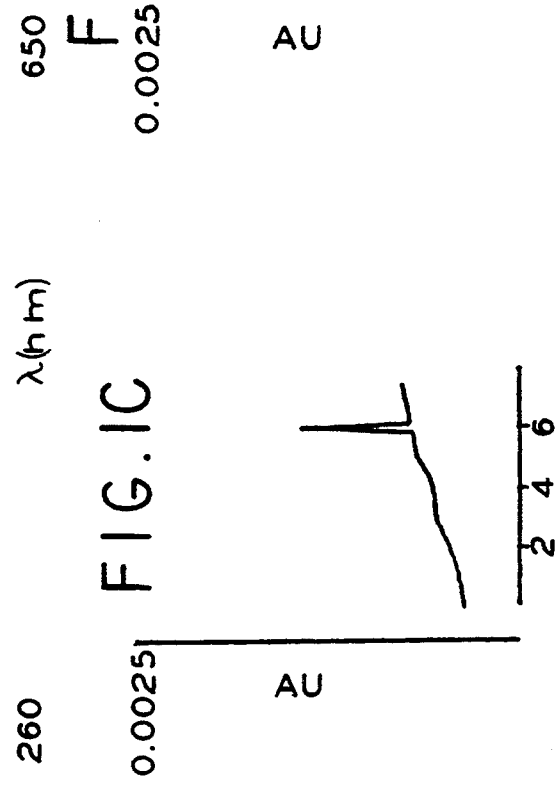

In the Saville reaction, the thiol/S-nitrosothiol stoichiometry was approximately 1.0. Capillary electrophoresis of samples revealed loss of the peak of homocysteine (5.94±0.15 min), as shown in FIG. 1C, with coincident generation of a new peak of slower electrophoretic mobility (7.74±0.18 min). The peak is identified as S-nitroso-homocysteine based on its theoretical predicted elution time of 7.2 minutes, determined from its charge to mass ratio (Grossman et al., Anal. Biochem. 179:28-33 (1989)), as shown in FIG. 1D. Importantly, HTL (FIG. 1E) was not present in reaction solutions. Taken together, these chemical data provide evidence for stoichiometric S-nitrosation of homocysteine.

To provide further support for the biological relevance of this reaction, S-nitroso-homocysteine was synthesized under physiologic conditions. In one method, S-nitrosation was achieved in homocysteine-saturated solutions (40 mM) of 0.5M or 1M sodium phosphate (pH 7.4) by brief exposure to authentic NO gas bubbled into solution. In other studies, homocysteine (1 mM) was incubated with endothelial cells stimulated in response to high shear stress to secrete EDRF, as previously described. In these experiments, endothelial cell chambers contained a total volume of 1 ml, 10 mM sodium phosphate buffered saline (pH 7.4) with an endothelial cell density of $5 \times 10^3$ cells/ul. Cells were exposed to a shear stress of approximately 0.43 dyne/cm$^2$ for 15 min (Stamler et al., Circ. Res. 65:789–795 (1989)).

Further studies were undertaken to elucidate the reactivity of sulfur, present in oxidized derivatives of homocysteine, such as thiolactone, toward $NO_x$.

Using the above nitrosation methods, it was determined that homocysteine-thiolactone does not react to form an S-nitrosothiol. Similarly, as determined by capillary zone electrophoresis (CZE), and in complementary Saville assays, the right sulfur of HTL is not amenable to electrophilic attack by $NO_x$.

Importantly, S-nitrosation of homocysteine prevented ring closure (thiolactone formation) in the acid catalyzed reaction. Incubations of homocysteine in acidic milieu (1–12N HCl) resulted in H+ concentration and time-dependent formation of HTL, which did not occur in the added presence of equimolar $NaNO_2$. Under these circumstances, S-nitroso-homocysteine formed, to the exclusion of HTL, and subsequent conversion to HTL was not observed over the time course of several hours as determined by CZE and in the Saville reaction. These data indicate that free sulfhydryl is a requirement for S-nitrosation, and suggest that S-nitroso-homocysteine formation and the oxidative pathways of homocysteine are biochemical reactions occurring exclusively of one another.

EXAMPLE 2:

The Effect of Homocysteine on the Endothelium a. Microcarrier Endothelial Cell Culture Endothelial cells, hereinafter referred to as "ECB's", were isolated from bovine aorta by established techniques (Schwartz, In Vitro 14:966–980 (1978)) and cultured on a microcarrier system of negatively charged spherical plastic beads, according to standard methods (Davies et al. J. Cell. Biol. 101:871–879 (1985)).

b. EDRF Generation from Cultured Cells

In this method, the endothelial cells were stimulated by high shear forces to secrete EDRF, using standard methods. In all experiments, prostanoid synthesis was inhibited with acetylsalicylic acid according to established protocol (Stamler et al., Circ. Res. 65:789–795 (1989); Cooke et al., Am. J. Physiol. 28:H804–H812 (1989)). For the purposes of this study, ECB were placed in chambers containing a total volume of 1 ml PBS (pH 7.4) at a density of $5 \times 10^3$ cells/ul, and exposed to a shear stress of 0.43 dyne/cm$^2$ for 15 minutes.

c. Endothelial Cell Viability

Assessments of cell growth and degree of endothelial cell confluence on microcarrier beads were routinely studied by phase-contrast microscopy. During the course of experiments, 25 ul aliquots of incubation medium were removed at hourly intervals for lactic dehydrogenase (LDH) measurements, determined spectroscopically with use of an LD-1 assay kit (Sigma Chemical Co.). At similar intervals, cell viability was assessed by vital dye exclusion with trypan blue.

In additional experiments endothelial cells (passages 6–20), isolated and grown as described above, were transferred after trypsin treatment, to 12-well tissue culture plates (Costar, Cambridge, Mass.), and grown to confluence in Dulbecco's Modified Eagles Medium (DMEM) supplemented with 10% calf serum. Immediately prior to experiments, individual wells were washed twice and filled with 750 ul of either Weymouth's medium or DMEM free of calf serum. Incubation with homocysteine (1–10 mM) in the presence and absence of $Cu^{2+}$ (1–50 uM), and $Fe^{2+}$ (10 uM), as well as various controls, were performed for up to 12 hours at 37° in 5% $CO_2$. At fixed intervals, viability was assessed by determination of LDH as described above, and by vital dye exclusion using trypan blue.

d. Morphological Studies

To complement tests of endothelial cell viability, cells were stained to visualize F-actin. The method used represents a minor modification of a previously published protocol (Phillips et al., J. Histochem. Cytochem. 36:551–554 (1988). Endothelial cells were grown to confluence in 6.5 mm, 24 well, Transwell polycarbonate cell cluster plates (tissue culture treated; 0.4 uM pore; nucleopore (R); Costar, Cambridge, Mass.). Equal volumes of homocysteine (1–10 mM), in the presence and absence of redox metals (1–50 uM $Cu^{2+}$ and $Fe^{2+}$), and control samples (DMEM) were added to the upper well compartments and incubated at 37° C. in 5% $CO_2$ atmosphere for up to 24 hours. At various time intervals, the polycarbonate membranes were removed, and the endothelial cell monolayers washed twice in PBS and fixed in 3.75% formaldehyde. The monolayers were subsequently washed and incubated with rhodamine-conjugated phalloidin (333 nM). The polycarbonate membranes were mounted on slides with a drop of glycerol/PBS (1:1) and epifluorescence microscopy performed with a Zeiss Axioscope microscope. Photographs were taken with a Kodak Ektachrome 400.

e. Endothelium-dependent Relaxation

The details of this standard bioassay have been reported previously (Osborne et al., J. Clin. Invest. 83:465–473 (1989)). Briefly, the descending thoracic aortae of New Zealand white female rabbits weighing 3–4 kg were isolated and cleaned of adherent connective tissue. In certain experiments, the endothelium was removed by the gentle rubbing with a cotton-tipped applicator inserted into the lumen. The rings were mounted on stirrups, suspended in oxygenated (95% $O_2$, 5% $CO_2$) glass chambers containing 7 ml of Kreb's buffer (pH 7.4) at 37° C., and connected to force transducers (model FTO3C) which recorded changes in isometric tension. Sustained contractions were induced with epinephrine, and endothelium-dependent relaxations induced with acetylcholine, thrombin and calcium ionophore. The effects of homocysteine on endothelium-dependent relaxations were examined in this model over a 10 hour period. In these experiments, homocysteine (1 mM) was added to the vessel chambers and endothelium-dependent relaxations compared to time-controls at hourly intervals.

In view of previous reports of homocysteine-mediated endothelial toxicity enhanced by redox metals (Starkebaum et al., J. Clin. Invest. 77:1370–1376 (1986)), 1 uM cuptic sulfate was added in selected experiments. Loss of free sulfhydryl was followed with Ellman's reagent (DTNB) (Sedlak et al., Anal. Biochem. 25:195–205 (1968)). Based on the determination of <20% oxidation of free sulfhydryl/hour, solutions of homocysteine were changed at hourly intervals.

In other experiments, the direct effects of homocysteine and S-nitroso-homocysteine on vessel tone were tested. These compounds were added to endothelium-denuded vessel rings after stable contractions to 1 uM epinephrine were achieved. In some cases, methylene blue (100 uM) was preincubated with vessel rings for 30 minutes prior to initiation of contractions.

f. Hydrogen Peroxide Generation from Homocysteine

There is strong evidence and agreement among studies that homocysteine injures endothelial cells by generating $H_2O_2$. It has been shown that the thiol autooxidizes in a two-electron transfer to $O_2$ with formation of $H_2O_2$ (Starkebaum et al., *J. Clin. Invest.* 77:1370–1376 (1986)). Therefore, the inventors tested the hypothesis that S-nitrosation, by blocking the SH group, would limit $H_2O_2$ generation.

Scopoletin serves as a hydrogen donor in the catalyzed reduction of $H_2O_2$ by horseradish peroxidase (HPO). In this oxidative reaction, scopoletin fluorescence is lost in direct proportion to $H_2O_2$ concentration in the medium (Root et al., *J. Clin. Invest.* 53:945–955 (1975)). The following assay conditions, designed to detect $H_2O_2$ production from homocysteine, have been published previously (Starkebaum et al., *J. Clin. Invest.* 77:1370–1376 (1986)). Reactions were performed in cuvettes containing 4 uM scopoletin in 2.5 ml Kreb's buffer, and were initiated by the addition of 2.2 uM HPO. Fluorescent measurements were performed on a spectrofluorimeter (Fluorolog 2 model F11 x; Spex Industries, Inc. Edison, N.J.) with sample excitations made at 360 nm and emission recorded at 460 nm.

Results are shown in FIG. 2 and Table 1. Notably, homocysteine induces a rapid loss of scopoletin fluorescence, thus indicating $H_2O_2$ generation.

g. Homocysteine-induced Endothelial Dysfunction

In the absence of enzymatic and morphological demonstration of homocysteine cytotoxicity, further confirmation of the above evidence for endothelial dysfunction in the vessel bioassay was pursued. The data, as shown in FIG. 3, demonstrate significant attenuation of endothelium-dependent relaxations in vessels exposed to homocysteine. Relaxations of S-nitroso-homocysteine-exposed vessels to 100 nm, 1 uM and 10 uM acetylcholine have been normalized to time controls in the absence of thiols for 5 experiments. Data are presented as mean ±S.D. Curves are each different from one another by ANOVA to p<. Moreover, the time course of homocysteine-induced endothelial dysfunction in this experiment corresponds well with the temporal profile of homocysteine-associated platelet activation as shown in FIG. 4. Endothelium-dependent relaxations induced by ADP and histamine were similarly diminished by homocysteine, thus excluding a selective muscarinic defect. Thus, these data provide a clear demonstration of homocysteine-mediated endothelial dysfunction, and strongly support the notion that this mechanism accounts for the platelet activation seen in the accompanying experiments.

In marked contrast, $H_2O_2$ production from S-nitroso-homocysteine is negligible, even in the presence of a metal catalyst. Thus, the cytotoxic mechanism of homocysteine through $H_2O_2$ production is attenuated by S-nitrosation.

EXAMPLE 3:

Effects of Homocysteine and S-nitroso-homocysteine on Platelet Aggregation a. Preparation of Platelets Venous blood was obtained from volunteers who had not consumed nonsteroidal antiinflammatory drugs for at least ten days, and was anticoagulated with 3.4 mM trisodium citrate. Platelet-rich plasma (PRP) was prepared by centrifugation at 150 g for 10 minutes at 25° C., and platelet-poor plasma (PPP) was prepared by centrifugation at 800 g for 10 minutes. Gel-filtered platelets (GFP) were obtained by passing PRP over a Sepharose-2B column in Tyrode's-Hepes buffer, as previously described (Hawiger et al., *Nature* 2831:195–198 (1980)). Platelet counts were measured using a Coulter counter (Model ZN, Coulter Electronics, Hialeah, Fla.) and were adjusted to 150,000/ul by the addition of PPP or HBS.

b. Platelet Aggregation

Aggregation of PRP and GFP was monitored using a standard nephelometric technique (Born et al., *J. Physiol* (London) 168:178–195 (1980)), in which 0.3 (GFP) or 0.5 (PRP) ml aliquots of platelets were incubated at 37% and stirred at 1000 rpm in a PAP-4 aggregometer (Biodata, Hatboro, Pa.). Aggregations were induced by the addition of varying concentrations of ADP (0.75 uM, 5 uM, 14 uM), thrombin (0.025 u/ml) and collagen (0.016 mg/ml, 0.16 mg/ml) and changes in light transmittance recorded.

In typical experiments, platelets were incubated with homocysteine and its derivatives for 3 minutes at 37° C. prior to the addition of agonist. In selected experiments, however, preincubations were made for up to one hour. Our methods for examining the effects of EDRF generated from ECBs on platelet aggregation have been published elsewhere in detail (Cooke et al., *Am. J. Physiol.* 28:H804–H812 (1989)). Notably, in these experiments, ECBs were preincubated in the presence and absence of homocysteine (5 mM) in DMEM for 6 hours, during which time, EDRF-mediated inhibition of platelet aggregation was assayed at hourly intervals. ECBs were washed with PBS to remove homocysteine prior to their incubation with platelets, and EDRF release was stimulated for 3 minutes by the effects of continuous stirring (flow) in the aggregometer (Cooke et al., *Am. J. Physiol.* 28:H804–H812 (1989)). Aggregations were then induced with 5 uM ADP. In all cases, aggregation was quantitated by measuring either the maximal rate of change or extent of change in light transmittance.

c. Effect of Homocysteine on Platelet Aggregation

The effects of homocysteine on platelet aggregation induced by ADP (14 uM) and collagen (0.16 mg/ml) are illustrated in FIG. 5. Experiments were performed in PRP taken from eight different volunteers, and unanimously exhibited dose-dependent inhibition of platelet aggregation. The IC50 for this inhibition is approximately 10 mM in the case of either agonist.

Additional experiments were performed, based on theoretical mechanisms proposed to explain the aggregation of platelets by synthetic thiols (Thomas et al., *Thromb Res.* 44:859–866 (1986); Zucker et al., Thromb. Haenostas (Stuttgarrt) 51:119–124 (1984)), such as oxyradical generation and nonspecific (presumably time-dependent) surface membrane disulfide reduction. The effects of homocysteine were further examined during incubations in PRP for up to one hour; using low doses of agonists (ADP, collagen and thrombin) that induce primary wave (reversible) aggregations; in GFP; and, after additional supplementation of PRP and GFP with $Cu^{2+}$ (1–10 uM) and $Fe^{2+}$ (1–10 uM) to facilitate SH-dependent superoxide and $H_2O_2$ generation. In all instances, agonist-induced aggregations were inhibited at millimolar concentrations of homocysteine and were largely unaffected at lower doses. In addition, spontaneous aggregations were not observed.

The effects of HTL (free base and hydrochloride) on ADP and collagen-induced platelet aggregation are also shown in FIGS. 5(A) and (B). The compound, in both forms, demonstrates weak antiplatelet activity. Notably, in these studies, stock solutions of the HTL free base were dissolved in 1N HCl, and similar results were demonstrated for the compound dissolved in DMSO.

Platelet aggregation induced by HTL (free base) in chloroform was shown recently (McCully et al., *Res. Comm. Chem. Path. Pharm.* 56(3):349–360 (1987)), and attributed to the membrane solubility of the compound in this solvent. In the experiments conducted by the inventors, control incubations with chloroform (HPLC grade) induced platelet aggregation at a vol % half that used by McCully et al. with no additional proaggregatory effect of HTL detectable, as shown in FIG. 6.

In other studies, the inventors induced acid-catalyzed conversion of homocysteine to HTL (6 N–12N HCl)) and tested the effects of HTL generated in this manner on platelet aggregation. The effects observed were analogous to those shown in FIG. 5. Homocystine and homocysteic acid had no effect on ADP (14 uM)-induced platelet aggregation in PRP at concentrations of up to 10 mM, confirming previous reports (McDonald et al., *Lancet* 1:745–746 (1964); McCully et al., *Res. Comm. Chem. Path. Pharm.* 56(3):349–360 (1987); Davis et al, *Am. J. Dis. Child* 129:1020–1021 (1975)).

d. EDRF and Homocysteine-Related Platelet Aggregation

In the absence of a detectable direct proaggregatory effect of homocysteine, we tested the hypothesis that homocysteine-mediated endothelial cell dysfunction leads secondarily to platelet activation.

For this purpose, ECB were incubated with homocysteine (5 mM, Weymouth's medium) for up to six hours; homocysteine was concomitantly excluded from the medium in time-control experiments. At regular intervals, ECB ($1 \times 10^6$ cells) were removed, washed in PBS, and added to platelet-rich plasma (PRP). EDRF secretion was stimulated in the aggregometer for 3 minutes (Cooke et al., *Am. J. Physiol.* 28:H804–H812 (1989)), and aggregation induced with ADP (5 uM).

As depicted in FIG. 4, prolonged exposure to homocysteine causes ECB to lose their innate capacity to inhibit platelet aggregation through secretion of EDRF. Measurements of LDH released into the medium showed small (<20%/6 hr) increases over time, and no difference between homocysteine-exposed and control ECBs. Similarly, no difference in cell detachment from microcarriers, or in trypan blue exclusion was detectable in the presence of homocysteine.

In additional studies of cell viability, endothelial cells were plated on microtiter plates and incubated with homocysteine (in the presence and absence of 1–10 uM $Cu^{2+}$) for up to 12 hours. Time-dependent increases in LDH were small (12+12%; mean +S.D., n=12) and again, not significantly increased above control levels by 10 mM homocysteine (N=12; p=N.S.). Staining of actin (n=3) revealed no detectable morphological changes in either the homocysteine-treated cells or the time-controls over 12 hours. These data, taken together, support the existence of a viable but dysfunctional, endothelium as a result of homocysteine exposure.

e. Effect of S-nitroso-homocysteine on Platelet Aggregation

As depicted in FIG. 7, S-nitroso-homocysteine markedly inhibited platelet aggregation. In control experiments using equivalent concentrations of $NaNO_2$, significant inhibition of platelet aggregation was not observed (normalized extent aggregation for $NaNO_2$ (100 uM)=1.02±0.12; n=12).

f. Effect of S-nitroso-homocysteine on Cyclic GMP Levels

Measurements of cyclic GMP (cGMP) were performed by radioimmunoassay on 400 ul aliquots of PRP and processed according to standard methods (Cooke et al., *Am. J. Physiol.* 28:H804–H812 (1989)). Incubations of homocysteine, S-nitroso-homocysteine, and other compounds of interest were made for 60 seconds and reactions were terminated by the addition of 10% trichloracetic acid.

Inasmuch as the antiplatelet effects of EDRF, NO and other nitroso-compounds are mediated through increases in intracellular cyclic GMP (Ignarro, *Circ. Res.* 65:1–21 (1989)), this mechanism was investigated for S-nitroso-homocysteine. Incubations of S-nitroso-homocysteine (100 uM) in PRP for 60 seconds resulted in 3.6-fold increases in intracellular platelet cyclic GMP above basal levels (p <0.05). Equivalent concentrations of $NaNO_2$ and homocysteine had no significant effect on platelet cyclic GMP (FIG. 8).

g. Formation of S-nitroso-homocysteine from EDRF and Platelet Inhibition

Eluent from ECB stimulation in response to high shear forces to secrete EDRF in the presence and absence of homocysteine (1 mM), were analyzed by the chemiluminescent and Saville methods for the formation of S-nitrosothiol. The results, shown in Table 2 and FIG. 9, demonstrate homocysteine-dependent formation of S-nitrosothiols, and quantitative concordance between the two methods of measurement; the greater variation among measurements in the method of Saville being accounted for by its more limited sensitivity (100 nM).

Figure 10A:
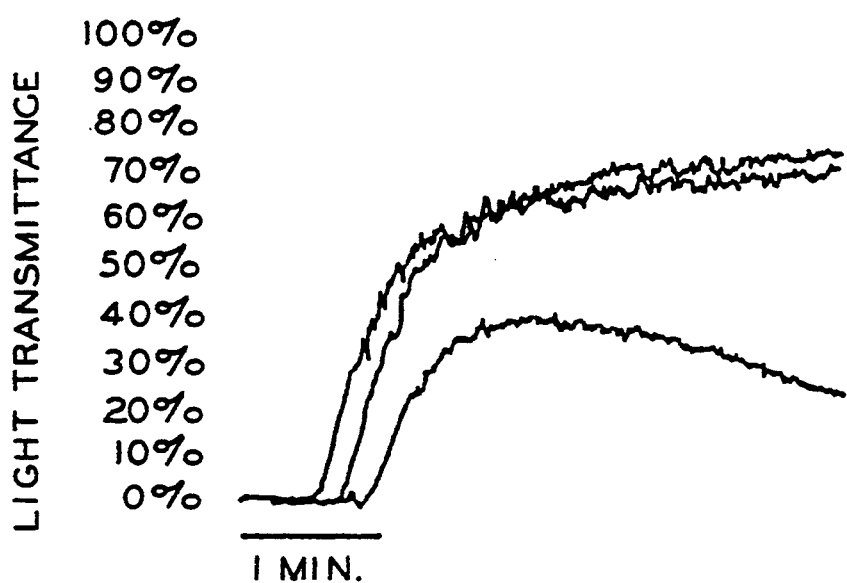
Figure 10B:
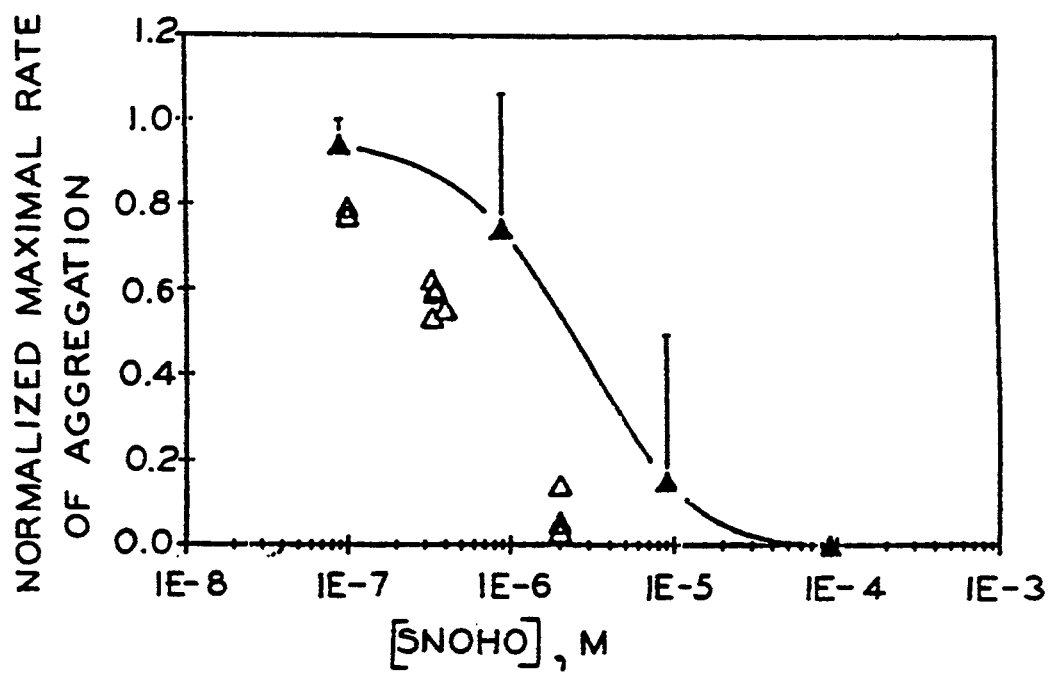

To further assay the bioactivity of these samples, 100 uL aliquots of ECB eluent were incubated with PRP (200 uL) for 10 minutes, and aggregations induced with ADP (5 uM). The platelet inhibition induced by ECB stimulated to secrete EDRF in the presence of homocysteine, is illustrated in FIG. 10A. As further evidence that S-nitroso-homocysteine is the active species in these studies, the degree of platelet inhibition observed corresponded with that predicted from the S-nitroso-homocysteine dose-response relationship (see FIG. 10B) based on the S-nitrosothiol content of solutions. Moreover, it is notable in the context of an EDRF half-life of 5–30 seconds (Palmer et al., *Nature* 327:524–526 (1987); Ignarro et al., *Proc. Natl. Acad. Sci., USA* 84:9265–9269 (1987)), that the time delay in ECB-eluent transfer to PRP in these studies was approximately 5 minutes, and that the bioactivity of samples was preserved with a 30 minute time delay as well (n=2).

As shown in FIG. 11, these findings are fully consistent with the remarkable stability of S-nitroso-homocysteine under physiologic conditions. Taken together, these experiments demonstrate that: 1) exposure of homocysteine to endogenous oxides of nitrogen results in the formation of S-nitroso-homocysteine; 2) brief exposure of endothelial cells to homocysteine engenders antiplatelet activity, through formation of S-nitroso-homocysteine; and 3) homocysteine may play an important role in preserving (stabilizing) NO and EDRF-like bioactivity in the formation of S-nitroso-homocysteine.

EXAMPLE 4:

Effect of S-nitroso-homocysteine on Vessel Relaxation

The effects of S-nitroso-homocysteine were further examined in the vessel bioassay according to methods described in Example 2(e). As illustrated in FIG. 12, the compound is an active vasodilator with an $IC_{50}$ of 150 nM (Table 3). Indicative of the potency of this S-NO adduct, the $IC_{50}$ of S-nitroso-cysteine in this system is 4 uM. Consistent with a cyclic GMP-dependent mechanism of action, relaxations by S-nitroso-homocysteine were entirely prevented by the guanylate cyclase inhibitor methylene blue.

EXAMPLE 5:

Effect of S-nitroso-homocysteine on $H_2O_2$ Generation

The methods described in Example 2(f) were employed to determine whether S-nitroso-homocysteine generates $H_2O_2$. The results are shown in FIG. 2. In marked contrast to homocysteine, $H_2O_2$ production from S-nitroso-homocysteine is negligible, even in the presence of a metal catalyst. Thus, the cytotoxic mechanism of homocysteine, mediated by $H_2O_2$ production, is attenuated by S-nitrosation.

EXAMPLE 6:

Effect of Cysteine On $H_2O_2$ Generation And Blockade of $H_2O_2$ Generation by , S-Nitrosation The methods described in Example 2(f) were employed to determine whether cysteine generates $H_2O_2$, and whether the $H_2O_2$ generation can be blocked by S-nitrosation. The results are shown in FIGS. 13 and 14. As shown in FIG. 13, cysteine induces a rapid loss of scopoletin fluorescence, thus indicating $H_2O_2$ generation. In contrast, as shown in FIG. 14, production of $H_2O_2$ from S-nitroso-cysteine is negligible. Thus, the cytotoxic mechanism of cysteine, mediated by $H_2O_2$-production, is attenuated by S-nitrosation.

DISCUSSION

Injury or dysfunction of the endothelium predisposes to thrombosis and vascular occlusive events. In these studies, the inventors observed progressive impairment in the capacity of the endothelium to maximally inhibit platelet aggregation during prolonged exposure to homocysteine, and demonstrated that homocysteine-mediated endothelial dysfunction predisposes to platelet activation. The data also concur with previous observations that the thrombotic tendencies in homocysteinemia do not impart a supranormal aggregation response.

The cytotoxicity and consequent thrombogenicity of homocysteine can be defined in terms of functional bioassay responses to EDRF. Thus, there is an inverse relationship between the capacity to secrete EDRF and a thrombogenic mechanism through platelet activation. However, this paradigm is further enlarged by the interaction between EDRF (or a derivative thereof) and homocysteine. Evidence suggests that other biological thiols react in the presence of $NO_x$ to form S-nitrosothiols and that biological thiols potentiate the bioactivity of EDRF.

To investigate further the potential importance of this interaction as pertains to homocysteine, the inventors synthesized and characterized the S-nitrosylated derivative, S-nitroso-homocysteine. Subsequent assays demonstrated the unusual stability of this S-nitrosothiol adduct under physiologic conditions vis-a-vis the half-life of NO, and that it possesses antiplatelet and vasodilatory properties mediated through increases in cyclic GMP.

In further support of biological relevance for S-nitroso-homocysteine, the inventors have documented homocysteine-dependent S-nitrosothiol formation from endogenously derived $NO_x$, and the antiplatelet bioactivity of this molecule. Thus the endothelium can counteract the thrombogenic mechanism of homocysteine through secretion of EDRF; the formation of S-nitroso-homocysteine is fundamental to this counter regulatory pathway. Endogenous formation of S-nitroso-homocysteine plays an integral role in the hemostatic process through platelet inhibition and vasorelaxation.

Homocysteine-induced endothelial injury in cell culture derives in large part, if not entirely, from $H_2O_2$, generated by way of the SH group. Inasmuch as biochemical measurements of $H_2O_2$ generation correlate directly with the cytotoxicity of homocysteine in these studies, it is noteworthy that S-nitrosation of homocysteine effectively inhibits sulfhydryl-dependent $H_2O_2$ generation. These observations, in conjunction with the demonstration of S-nitroso-homocysteine formation in the presence of EDRF, describe a novel mechanism by which the endothelium modifies the toxicity of homocysteine, as well as other sulfur-containing amino acids. In this context, moreover, the atherogenicity of homocysteine imparted by its oxidative metabolism to a thiolactone is accounted for, at least in part, by the inaccessibility of lactone sulfur (in an ester linkage) to electrophilic attack by $NO_x$.

The toxic manifestations of homocysteine reflect an imbalance between NO availability and homocysteine levels. Accordingly, an NO-deficit provides a more accurate measure of the pathogenic potential of homocysteine than the absolute level of "thiol excess". Thus, hyperhomocysteinemia reflects a relative deficiency of NO (as a result of endothelial injury), as well as an elevation of homocysteine levels resulting from the more classic acquired deficiencies, or inborn errors of its metabolism. The mechanism of hyperhomocysteinemia notwithstanding, the resultant endothelial damage impedes NO production and interferes with the normal antithrombotic mechanisms of the endothelium. This triggers a cycle in which these antithrombotic cytoprotective mechanisms of S-nitrosation are increasingly compromised at the expense of a predisposition to atherosclerosis and thrombosis, as depicted in FIG. 15.

FIG. 15 depicts a mechanism of homocysteine-mediated atherothrombosis and its modulation of NO. 1) homocysteine reacts with $NO_x$ derived from the endothelium to form a vasodilatory, antiplatelet S-nitrosothiol adduct. 2) S-nitroso-homocysteine is one of several potential biological S-nitrosothiols which may react through thiol-nitrosothiol exchange to serve as a pool of molecules active for relaxation and platelet inhibition in plasma and the cell cytosol. 3) In disease states in which homocysteine levels are elevated or NO release is compromised, homocysteine (free SH) damages endothelium through generation of $H_2O_2$ thereby inhibiting NO production; by a similar oxy-radical-dependent mechanism, homocysteine partakes in oxidation of LDL to an atherogenic form recognized by the scavenger receptor. 4) With a relative NO deficit, homocysteine is shunted toward oxidative metabolism by way of HTL; this pathway leads to further vessel wall damage at least in part, through excessive sulfuration of connective tissues.

In a broader context, the cytoprotective mechanism of S-nitrosation plays a more general role in modulating the atherogenicity of other sulfur-containing amino acids, such as cysteine. There is increasing evidence that thiol-dependent atherogenic mechanism(s) are not specific to homocysteine. Cysteine also supports the generation of reactive oxygen species ($O_{\cdot 2}$) which have been strongly implicated in atherogenesis through modification of low density lipoproteins to a form recognized by the scavenger receptor (Parthasarathy, S. Biochim. Biophys. Acta 917:337–340 (1987); Heinecke, et al. J. Biol. Chem. 262:10098–10103 (1987)). Cysteine is also a highly efficient two-electron donor in the copper catalyzed reaction, producing $H_2O_2$. The unappreciated toxicity of cysteine is especially pertinent in this context, because the vasodilatory and antiplatelet properties of the S-nitrosated derivative of this molecule have been important considerations in the claims for its identity as EDRF.

Therefore, there is a need for regulatory control of the biochemical pathways of sulfur amino acids, in general, to modify their cytotoxic and thrombogenic potential. As demonstrated with respect to homocysteine, S-nitrosation represents one such cell regulatory mechanism that simultaneously confers upon biological thiols, EDRF-Like bioactivity, and attenuates their toxic effects.

In summary, the data presented show the following: 1) homocysteine and HTL are weak platelet inhibitors and do not directly promote platelet aggregation; 2) homocysteine-mediated endothelial injury, with consequent attenuation of EDRF/$NO_x$ production, predisposes to platelet activation; 3) homocysteine reacts with oxides of nitrogen under physiologic conditions to form a stable S-nitrosothiol (S-nitroso-homocysteine); 4) with oxidative metabolism of homocysteine, the potential for S-nitroso-homocysteine formation is lost; 5) the mechanism of homocysteine-mediated endothelial injury through generation of reactive oxygen species does not occur in the presence of S-nitroso-homocysteine; and 6) S-nitroso-homocysteine possesses intrinsic EDRF-like antiplatelet and vasodilatory properties mediated through cyclic GMP.

These data provide new insight into the mechanism of homocysteine-induced atherosclerosis and thrombosis, and highlight the larger potential of the S-nitrosothiol functionality in regulation of cellular biochemistry and metabolism. The concept that NO availability is of central importance to the thrombogenic and cytotoxic potential of homocysteine has important pharmacological implications as well. Thus, the provision of NO equivalents is therapeutically important in the treatment or prevention of disease states in which homocysteine plays a pathogenic role.

TABLE 1

$H_2O_2$ GENERATION BY HOMOCYSTEINE AND S—NO-HOMOCYSTEINE

| | Initial Rates of $H_2O_2$ Generation (uM/min) |
|---|---|
| Homocysteine (500 uM) | 0.11 ± 0.04 |
| Homocysteine (500 uM) + $CU^{2+}$ (5 uM) | 0.165 ± 0.013 |
| S—NO-Homocysteine (500 uM) | 0 |
| S—NO-Homocysteine (500 uM) + $Cu^{2+}$ (5 um) | 0 |

$H_2O_2$ generation was determined from loss of scopoletin fluorescence as described in Methods. Values are presented as mean ± S.D., n = 3.

TABLE 2

S—NO-HOMOCYSTEINE FORMATION FROM EDRF AND HOMOCYSTEINE

| | TOTAL NO | 5-Nitrosothiol |
|---|---|---|
| Seville | 1.5 ± 0.64 μm | 0.92 ± 0.43 μm |
| Chemilum | 1.32 ± 0.37 μm | 0.81 ± 0.24 μm |

Legend: Endothelial cells were stimulated by high shear forces to see EDRF as described in Methods. NO generation (bound as RS—NO free in solution) and SNOHO formation were assayed by Saville method and by modified chemiluminescence. Results presented at mean ± S.D, n = 5–10.

TABLE 3

VASORELAXATION BY S—NO-HOMOCYSTEINE % RELAXATION

| | $NaNO_2$ | homocysteine | SNOHO |
|---|---|---|---|
| 15 nM | 0 | 0 | 6 ± 4% |
| 150 nM | 0 | 0 | 33 ± 10% |
| 1–5 μm | 7 ± 7% | 0 | 85 ± 3% |

Legend: Relaxant properties of S-nitroso-homocysteine synthesized from homocysteine and $NaNO_2$. Values expressed as mean ± S.D., n = 3.

What is claimed is:

1. A method for treatment or prevention of hyperhomocysteinemia, comprising
    administering an amount effective to treat or prevent hyperhomocysteinemia of a compound selected from the group consisting of S-nitroso-N-acetyl-cysteine, S-nitroso-glutathione, S-nitroso-cysteine, S-nitroso-homocysteine and S-nitroso-captopril to an individual who has or is to be prevented from having hyperhomocysteinemia.

2. The method of claim 1 wherein said compound is administered as part of a pharmaceutical composition comprising a pharmaceutically acceptable carrier.

3. The method of claim 2, wherein said pharmaceutical composition is administered to a patient by a route comprising oral, sublingual, intravenous, intramuscular or aerosol delivery.

4. The method of claim 1 wherein said compound is S-nitroso-homocysteine.

* * * * *